US011078464B2

(12) United States Patent
Zhao et al.

(10) Patent No.: US 11,078,464 B2
(45) Date of Patent: Aug. 3, 2021

(54) HIGH TITER RECOMBINANT AAV VECTOR PRODUCTION IN ADHERENT AND SUSPENSION CELLS

(71) Applicant: AMGEN INC., Thousand Oaks, CA (US)

(72) Inventors: Huiren Zhao, Thousand Oaks, CA (US); Grace Ki Jeong Lee, Simi Valley, CA (US); Thomas Wolfe, Simi Valley, CA (US); Cherylene Plewa, Simi Valley, CA (US); Jackie Z. Sheng, Thousand Oaks, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 14/915,630

(22) PCT Filed: Aug. 28, 2014

(86) PCT No.: PCT/US2014/053281
§ 371 (c)(1),
(2) Date: Feb. 29, 2016

(87) PCT Pub. No.: WO2015/031686
PCT Pub. Date: Mar. 5, 2015

(65) Prior Publication Data
US 2016/0222356 A1 Aug. 4, 2016

Related U.S. Application Data

(60) Provisional application No. 61/872,523, filed on Aug. 30, 2013.

(51) Int. Cl.
*C12N 7/00* (2006.01)
*C12N 15/86* (2006.01)

(52) U.S. Cl.
CPC ............... *C12N 7/00* (2013.01); *C12N 15/86* (2013.01); *C12N 2750/14143* (2013.01); *C12N 2750/14151* (2013.01); *C12N 2750/14152* (2013.01)

(58) Field of Classification Search
CPC ............ C12N 7/00; C12N 15/86; C12N 2750/14143; C12N 2750/14151; C12N 2750/14152
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,139,941 A | 8/1992 | Muzyczka et al. |
| 5,173,414 A | 12/1992 | Lebkowski et al. |
| 5,302,697 A | 4/1994 | Goodey et al. |
| 5,399,346 A | 3/1995 | Anderson et al. |
| 5,633,162 A | 5/1997 | Keen et al. |
| 5,658,776 A * | 8/1997 | Flotte ............... C12N 15/86 435/320.1 |
| 6,001,650 A | 12/1999 | Colosi |
| 6,004,797 A | 12/1999 | Colosi |
| 6,022,952 A | 2/2000 | Weiner et al. |
| 6,156,303 A | 12/2000 | Russell et al. |
| 6,335,178 B1 | 1/2002 | Weiner et al. |
| 6,376,237 B1 | 4/2002 | Colosi |
| 6,383,794 B1 * | 5/2002 | Mountz ............... C12N 15/86 435/235.1 |
| 6,387,670 B1 * | 5/2002 | Leblois-Prehaud .... C12N 15/86 424/93.2 |
| 6,566,118 B1 * | 5/2003 | Atkinson ............... C07C 2/32 435/235.1 |
| 6,924,128 B2 * | 8/2005 | Allen ............... C07K 14/4712 424/93.2 |
| 6,989,264 B2 * | 1/2006 | Atkinson ............ A61K 48/0091 435/239 |
| 6,995,006 B2 * | 2/2006 | Atkinson ............ A61K 48/0091 435/235.1 |
| 7,029,909 B1 | 4/2006 | Uemura et al. |
| 7,091,029 B2 * | 8/2006 | Hwang ............... C07K 14/005 424/93.2 |
| 8,007,780 B2 | 8/2011 | Arbetman et al. |
| 2002/0127582 A1 * | 9/2002 | Atkinson ............ A61K 48/0091 435/6.11 |
| 2002/0160501 A1 * | 10/2002 | Atkinson ............ A61K 48/0091 435/239 |

(Continued)

FOREIGN PATENT DOCUMENTS

| | | | |
|---|---|---|---|
| WO | WO 1987/00195 A1 | 1/1987 | |
| WO | WO-9003430 A1 * | 4/1990 | ........... C12N 5/0037 |

(Continued)

OTHER PUBLICATIONS

AAV Helper Free Expression System. Cell Biolabs Inc. http://www.cellbiolabs.com/sites/default/files/VPK-402-aav-helper-free-expression-system.pdf. Accessed online Jan. 2, 2017.*

AAV Helper Free Expression System. Cell Biolabs, Inc. Accessed via Wayback Machine, Internet Archive. Posted Dec. 5, 2012. http://www.cellbiolabs.com/aav-helper-free-packaging-system.*

Huang X, Hartley AV, Yin Y, Herskowitz JH, Lah JJ, Ressler KJ. AAV2 production with optimized N/P ratio and PEI-mediated transfection results in low toxicity and high titer for in vitro and in vivo applications. J Virol Methods. Nov. 2013;193(2):270-7. doi: 10.1016/j.jviromet.2013.06.008.*

ThermoFisher Scientific. FREESTYLE™ 293 Expression System. https://www.thermofisher.com/US/en/home/references/protocols/cell-culture/transfection-protocol/freestyle-293-expression-system.html#3. Mar. 15, 2007.*

(Continued)

*Primary Examiner* — Rachel B Gill
(74) *Attorney, Agent, or Firm* — Jonathan M. Dermott

(57) ABSTRACT

The present invention is directed to an in vitro method of producing a recombinant AAV virion in a mammalian host cell that comprises a functional adenoviral E1A gene and rAAV virions made by the method. Host cells are transfected with varying ratios of plasmids comprising the E1A gene and virions.

14 Claims, 23 Drawing Sheets

Specification includes a Sequence Listing.

(56) References Cited

U.S. PATENT DOCUMENTS

| | | | |
|---|---|---|---|
| 2003/0022356 A1* | 1/2003 | Leblois-Prehaud | C12N 15/86 435/235.1 |
| 2003/0104400 A1 | 6/2003 | Ruben et al. | |
| 2003/0175974 A1* | 9/2003 | Allen | C07K 14/4712 435/457 |
| 2004/0058439 A1* | 3/2004 | Hwang | C07K 14/005 435/320.1 |
| 2004/0197895 A1* | 10/2004 | Kotin | C07K 14/005 435/235.1 |
| 2005/0148076 A1* | 7/2005 | Allen | C07K 14/4712 435/456 |
| 2005/0266567 A1* | 12/2005 | Atkinson | A61K 48/0091 435/456 |
| 2007/0026521 A1* | 2/2007 | Colosi | C07K 14/005 435/456 |
| 2008/0206812 A1* | 8/2008 | Atkinson | A61K 48/0091 435/69.1 |
| 2009/0017542 A1* | 1/2009 | Colosi | C07K 14/005 435/455 |
| 2010/0173979 A1* | 7/2010 | Dodge | C12N 15/86 514/44 R |
| 2010/0248355 A1* | 9/2010 | Atkinson | A61K 48/0091 435/320.1 |

FOREIGN PATENT DOCUMENTS

| | | | |
|---|---|---|---|
| WO | WO 1992/01070 A1 | 1/1992 | |
| WO | WO 1993/03769 A1 | 3/1993 | |
| WO | WO 1997/17458 A1 | 5/1997 | |
| WO | WO 1999/14354 A1 | 3/1999 | |
| WO | WO 2001/83797 A2 | 11/2001 | |
| WO | WO 2013063379 A1 * | 5/2013 | C12N 7/00 |

OTHER PUBLICATIONS

Hayes S. Optimising Transfection Performance. https://www.mirusbio.com/assets/misc_technical_documents/optimising_transfection_performance.pdf. Innovations in Pharmaceutical Technology, pp. 74-76. Oct. 23, 2010.*

Collaco RF, Cao X, Trempe JP. A helper virus-free packaging system for recombinant adeno-associated virus vectors. Gene. Oct. 1, 1999;238(2):397-405.*

Chirico J, Trempe JP. Optimization of packaging of adeno-associated virus gene therapy vectors using plasmid transfections. J Virol Methods. Dec. 1998;76(1-2):31-41.*

Shin JH, Yue Y, Duan D. Recombinant adeno-associated viral vector production and purification. Methods Mol Biol. 2012;798:267-84.*

Li C, Samulski RJ. Serotype-specific replicating AAV helper constructs increase recombinant AAV type 2 vector production. Virology. Apr. 2, 2005;335(1):10-21.*

Tullis GE, Shenk T. Efficient replication of adeno-associated virus type 2 vectors: a cis-acting element outside of the terminal repeats and a minimal size. J Virol. Dec. 2000;74(24):11511-21.*

Wright JF. Transient transfection methods for clinical adeno-associated viral vector production. Hum Gene Ther. Jul. 2009;20(7):698-706.*

Grieger JC, Soltys SM, Samulski RJ. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-297. doi: 10.1038/mt.2015.187. Epub Oct. 6, 2015.*

Xiao X, Li J, Samulski RJ. Production of high-titer recombinant adeno-associated virus vectors in the absence of helper adenovirus. J Virol. Mar. 1998;72(3):2224-32.*

Huang X, Hartley AV, Yin Y, Herskowitz JH, Lah JJ, Ressler KJ. AAV2 production with optimized N/P ratio and PEI-mediated transfection results in low toxicity and high titer for in vitro and in vivo applications. J Virol Methods. Nov. 2013;193(2):270-7. doi: 10.1016/j.jviromet.2013.06.008. Epub Jun. 19, 2013.*

Reed SE, Staley EM, Mayginnes JP, Pintel DJ, Tullis GE. Transfection of mammalian cells using linear polyethylenimine is a simple and effective means of producing recombinant adeno-associated virus vectors. J Virol Methods. Dec. 2006;138(1-2):85-98. Epub Sep. 6, 2006.*

Maurisse R, De Semir D, Emamekhoo H, Bedayat B, Abdolmohammadi A, Parsi H, Gruenert DC. Comparative transfection of DNA into primary and transformed mammalian cells from different lineages. BMC Biotechnol. Feb. 8, 2010;10:9.*

Dong W, Li S, Jin G, Sun Q, Ma D, Hua Z. Efficient Gene Transfection into Mammalian Cells Mediated by Cross-linked Polyethylenimine. Int J Mol Sci. 2007;8(2):81-102. Published Feb. 14, 2007.*

Longo PA, Kavran JM, Kim MS, Leahy DJ. Transient mammalian cell transfection with polyethylenimine (PEI). Methods Enzymol. 2013;529:227-40.*

Huang X, Hartley AV, Yin Y, Herskowitz JH, Lah JJ, Ressler KJ. AAV2 production with optimized N/P ratio and PEI-mediated transfection results in low toxicity and high titer for in vitro and in vivo applications. J Virol Methods. Nov. 2013;193(2):270-7. Epub Jun. 19, 2013.*

Delafosse L, Xu P, Durocher Y. Comparative study of polyethylenimines for transient gene expression in mammalian HEK293 and CHO cells. J Biotechnol. Jun. 10, 2016;227:103-111. Epub Apr. 13, 2016 (Year: 2016).*

Nyamay'Antu A, Kedinger V, Erbacher P. Addressing scaling-up limitations: optimized PEI-mediated production of clinical grade viral vectors. Cell & Gene Therapy Insights. Feb. 22, 2018, pp. 73-79. (Year: 2018).*

Addgene. "AAV Production in HEK293T Cells." Updated May 24, 2019; https://www.addgene.org/protocols/aav-production-hek293-cells/). (Year: 2019).*

Tom R, Bisson L, Durocher Y. Transfection of HEK293-EBNA1 Cells in Suspension with Linear PEI for Production of Recombinant Proteins. CSH Protoc. Mar. 1, 2008;2008:pdb.prot4977.) (Year: 2008).*

Markakis EA, Vives KP, Bober J, Leichtle S, Leranth C, Beecham J, Elsworth JD, Roth RH, Samulski RJ, Redmond DE Jr. Comparative transduction efficiency of AAV vector serotypes 1-6 in the substantia nigra and striatum of the primate brain. Mol Ther. Mar. 2010;18(3):588-93. Epub Dec. 15, 2009. (Year: 2009).*

Park JY, Lim BP, Lee K, Kim YG, Jo EC. Scalable production of adeno-associated virus type 2 vectors via suspension transfection. Biotechnol Bioeng. Jun. 20, 2006;94(3):416-30. (Year: 2006).*

Hildinger M, Baldi L, Stettler M, Wurm FM. High-titer, serum-free production of adeno-associated virus vectors by polyethyleneimine-mediated plasmid transfection in mammalian suspension cells. Biotechnol Lett. Nov. 2007;29(11): 1713-21. Epub Jul. 17, 2007. (Year: 2007).*

Durocher Y, Pham PL, St-Laurent G, Jacob D, Cass B, Chahal P, Lau CJ, Nalbantoglu J, Kamen A. Scalable serum-free production of recombinant adeno-associated virus type 2 by transfection of 293 suspension cells. J Virol Methods. Sep. 2007;144(1-2):32-40. Epub Apr. 30, 2007. (Year: 2007).*

Grieger JC, Soltys SM, Samulski RJ. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-297. Epub Oct. 6, 2015. (Year: 2015).*

Zhao H, Lee KJ, Daris M, Lin Y, Wolfe T, Sheng J, Plewa C, Wang S, Meisen WH. Creation of a High-Yield AAV Vector Production Platform in Suspension Cells Using a Design-of-Experiment Approach. Mol Ther Methods Clin Dev. Jun. 3, 2020;18:312-320. (Year: 2020).*

Chahal PS, Schulze E, Tran R, Montes J, Kamen AA. Production of adeno-associated virus (AAV) serotypes by transient transfection of HEK293 cell suspension cultures for gene delivery. J Virol Methods. Feb. 2014;196:163-73. Epub Nov. 13, 2013. (Year: 2013).*

Aslanidi, G. et al., "An inducible system for high efficient production of recombinant production of recombinant adeno-associated virus (rAAV) vectors in insect Sf9 cells," *Proc. Natl Acad. Sci. USA* 106:5059-5064 (2009).

(56) References Cited

OTHER PUBLICATIONS

Barnes, D. et al., "Methods for growth of cultured cells in serum-free medium," *Anal. Biochem.* 102: 255-270 (1980).
Berger, S. L. and Kimmel, A. R., *Methods in Enzymology: Guide to Molecular Cloning Techniques*, vol. 152, Academic Press, Inc., San Diego, Calif. (1987) (Table of Contents Only).
Berns, K. I. and Bohenzky, R. A., "Adeno-associated viruses: an update," *Advances in Virus Research*, 32:243-307 Academic Press, Inc. (1987).
Berns, K. I., "Parvoviridae and their Replication" *Fundamental Virology*, B. N. Fields and D. M. Knipe eds., 2d ed., Raven Press, New York, Chapter 32, 817-837 (1991).
Berns K, and Parrish C. R., "*Parvoviridae*" *Fields Virology*, 5th ed. Ed. by David M. Knipe, Wolters Kluwer/Lippincott Williams & Wilkins, Philadelphia, pp. 1-78 (2007).
Booth, M. J. et al., "Transfection-free and scalable recombinant AAV vector production using HSV/AAV hybrids", *Gene Ther.* 11: 829-837 (2004).
Carter, B. J. et al, "Properties of an Adenovirus Type 2 Mutant, Ad2dl807, Having a Deletion near the Right-Hand Genome Terminus: Failure to Help AAV Replication," *Virology* 126: 505-516 (1983).
Carter, B. J., "Adeno-Associated Virus Helper Functions," P. Tijssen, PhD, ed., *CRC Handbook of Parvoviruses*, vol. I, Chapter 13, pp. 255-282 (1990).
Carter, B. J., "Adeno-associated virus vectors," *Current Opinion in Biotechnology* 3: 533-539 (1992).
Chu, G. et al. "Short Communication SV40 DNA transfection of cells in suspension: analysis of the efficiency of transcription and translation of T-antigen," *Gene*, 13: 197-202 (1981).
Dos Santos Coura, R. and Nardi, N. B., "The state of the art of adeno-associated virus-based vectors in gene therapy," *Virology J.* 4: 99-105 (2007).
Davis, L G. et al. Methods in Molecular Biology, Elsevier Science Publishing Co., Inc. (1986) (Table of Contents Only).
Durocher, Y. et al., "Scalable serum-free production of recombinant adeno-associated virus type 2 by transfection of 293 suspension cells," *J. Virol. Methods, Elsevier BV, NL.* 144(1-2): 32-40 (2007).
Engels, J. W. et al. "Gene Synthesis," *Angew. Chem. Int. Ed. Engl.*, 28: 716-734 (1989).
Farson, D. et al., "Development and characterization of a cell line for large-scale, serum-free production of recombinant adeno-associated viral vectors," *J Gene Med.* 6(12): 1369-1381 (2004).
Feng, L et al., "Improvement in the suspension-culture production of recombinant adeno-associated virus-LacZ in HEK-293 cells using PEI-DNA complexes in combination with hypothermic treatment," *Biotechnol Appl Biochem.* 50: 121-132 (2008).
Flotte, T. R. et al., "An improved system for packaging recombinant adeno-associated virus vectors capable of in vivo transduction," Gene Therapy, 2(1):29-37 (1995).
Gao, G-P. et al., "High-titer adeno-associated viral vectors from a Rep/Cap cell line and hybrid shuttle virus," *Hum. Gene Ther.* 9: 2353-2362 (1998).
Graham, F. L. et al. "A New Technique for the Assay of Infectivity of Human Adenovirus 5 DNA," *Virology* 52: 456-467 (1973).
Graham, F. L. et al., "Characteristics of a Human Cell Line Transformed by DNA from Human Adenovirus Type 5," *J. Gen. Virol.*, 36: 59-74 (1977).
Grimm, D. et al., RNAi and Gene Therapy: A Mutual Attraction, *Hematology, Am Soc Hematol Educ Program.*: 473-481 (2007).
Guss, B. et al., "Structure of the IgG-binding regions of streptococcal protein G," *EMBO J.* 5(7): 1567-1575 (1986).
Ham, R. G. et al., "Media and Growth Requirements," *Meth. Enz.* 58: 44-93 (1979).
Handa, et al., "Complementation of adeno-associated virus growth with temperature-sensitive mutants of human adenovirus types 12 and 5," *J. Gen. Virol.* 29: 239-242 (1975).
Hildinger, M. et al., "High-titer, serum-free production of adeno-associated virus vectors by PEI-mediated plasmid transfection in mammalian suspension cells," *Biotechnol. Lett. Springer Netherlands, Dordrecht*, 29(11): 1713-1721 (2007).
Ishibashi et al, "The potentiation of type 1 adeno-associated virus by temperature-sensitive conditional-lethal mutants of CELO virus at the restrictive temperature," *Virology* 45: 317-320 (1971).
Ito, M. et al., "Adeno-associated satellite virus growth supported by a temperature-sensitive mutant of human adenovirus," *J. Gen. Virol.* 9: 243-245 (1970).
Janik, J. E. et al., "Locations of adenvirus genes required for the replication of adenovirus-associated virus," *Proc. Natl. Acad. Sci. USA* 78(3): 1925-1929 (1981).
Jay, F. T. et al., "Eukaryotic translational control: Adeno-associated virus protein synthesis is affected by a mutation in the adenovirus DNA-binding protein," *Proc. Natl. Acad. Sci. USA* 78(5): 2927-2931 (1981).
Joshua, C.G. et al., "Packaging capacity of adeno-associated virus serotypes: Impact of larger genomes on infectivity and postentry steps," *J. Virol.*, 79: 9933-9944 (2005).
Khan, I. F. et al., "AAV-mediated gene targeting methods for human cells," *Nature Protocols* 6(4): 482-501 (2011).
Kotin, R. M., "Prospects for the use of adeno-associated virus as a vector for human gene therapy," *Human Gene Therapy* 5: 793-801 (1994).
Laughlin, C. A. et al., "Effect of deletions in adenovirus early region 1 genes upon replication of adeno-associated virus," *J. Virol*, 41(3): 868-876 (1982).
Lebkowsk, J. S.i et al., "Adeno-associated virus: a vector system for efficient introduction and integration of DNA into a variety of mammalian cell types," *Molec. Cell. Biol.*, 8(10): 3988-3996 (1988).
Lindmark, R. et al., "Binding of immunoglobulins to protein A and immunoglobulin levels in mammalian sera," *J. Immunol. Meth.*, 62: 1-13 (1983).
Lock, M. et al, "Rapid, simple, and versatile manufacturing of recombinant adeno-associated viral vectors at scale," *Hum. Gene Ther.*, 21: 1259-1271 (2010).
Maniatis, T. et al., "Regulation of inducible and tissue-specific gene expression," *Science* 236: 1237-1244 (1987).
Mather, J. P., "Establishment and characterization of two distinct mouse testicular epithelial cell lines," *Biol. Reprod.*, 23: 243-252 (1980).
Mather, J. P. et al., "Culture of testicular cells in hormone-supplemented serum-free medium," *Annals N.Y Acad Sci.* 383: 44-68 (1982).
Matshushita, T. et al., "Adeno-associated virus vectors can be efficiently produced without helper virus," *Gene Therapy*, 5:938-945 (1998).
McCarty, D. M. et al., "Sequences required for coordinate induction of adeno-associated virus p19 and p40 promoters by rep protein," *J. Virol.*, 65(6): 2936-2945 (1991).
Miller, D. G., "AAV-mediated gene targeting," *Methods Mol Biol.*, 807: 301-315 (2011).
Miyazaki, Y. et al., "Viral delivery of miR-196a ameliorates the SBMA phenotype via the silencing of CELF2," *Nat Med.* 18: 1136-1141 (2012).
Muzyczka, L., "Use of adeno-associated virus as a general transduction vector for mammalian cells," *Current Topics in Microbiol. and Immunol.* 158: 97-129 (1992).
Myers et al., "Adenovirus helper function for growth of adeno-associated virus: Effect of temperature-sensitive mutations in adenovirus early gene region 2," *J. Virol.* 35(1): 65-75 (1980).
Myers et al., "Adeno-associated virus replication," *J. Biol. Chem.* 256(2): 567-570 (1981).
Nizzardo, M. et al., "Research advances in gene therapy approaches for the treatment of amyotrophic lateral sclerosis," *Cell Mol Life Sci.* 69:1641-1650 (2012).
Ostrove, J. M. et al., "Adenovirus Early Region 1b Gene Function Required for Rescue of Latent Adeno-Associated Virus," *Virology*, 104: 502-505 (1980).
Palermo, D. P. et al., "Production of analytical quantities of recombinant proteins in Chinese hamster ovary cells using sodium butyrate to elevate gene expression," *J Biotechnol.* 19: 35-47 (1991).

(56) References Cited

OTHER PUBLICATIONS

Park, J. Y. et al., "Scalable production adeno-associated virus type 2 vectors via suspension transfection," *Biotech. Bioeng.* 94: 416-430 (2006).

Pham, P. L. et al., "Transient gene expression in HEK293 cells: peptone addition post-transfection improves recombinant protein synthesis," *Biotechnol. & Bioeng.* 90(3): 332-344 (2005).

Sambrook, J. et al. *Molecular Cloning, A Laboratory Manual*, vols. 1-3, Cold Spring Harbor Laboratory Press, Cold Spring Harbor, New York (1989) (Table of Contents Only).

Samulski, R. J. et al., "Adenovirus E1B 55-$M_r$ polypeptide facilitates timely cytoplasmic accumulation of adeno-associated virus mRNAs," *J. Virol.* 62: 206-210 (1988).

Samulski, R. J. et al., "Helper-free stocks of recombinant adeno-associated viruses: Normal integration does not require viral gene expression," *J. Virol.* 63: 3822-3828 (1989).

Sanger, F. et al. "DNA sequencing with chain-terminating inhibitors," *Proc. Natl. Acad. Sci. USA*, 74: 5463-5467 (1977).

Schlehofer, J. R. et al., "Vaccinia virus, herpes simplex virus, and carcinogens induce DNA amplification in a human cell line and support replication of a helpervirus dependent parvovirus," *Virology* 152: 110-117 (1986).

Schwartz, R. M. and Dayhoff, M.O. et al, Chapter 23, "Matrices for Detecting Distant Relationships," *Atlas of Protein Sequence and Structure*, 5(3): 353-358, National Biomedical Research Foundation, Washington D.C. U.S.A (1978).

Smith, T. F. and Waterman, M. S., "Comparison of Biosequences," *Advances in Appl. Math.*, 2: 482-489 (1981).

Strauss, S. E. et al., "DNA-minus temperature-sensitive mutants of adenovirus type5 help adenovirus-associated virus replication," *J. Virol.* 17(1): 140-148 (1976).

Thomson, B. J. et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression," *Virology* 204: 304-311 (1994).

Thorne, B. A. et al., "Manufacturing recombinant adeno-associated viral vectors from producer cell clones," *Hum. Gene Ther.* 20: 707-714 (2009).

Toublanc, E. et al., Identification of a replication-defective herpes simplex virus for recombinant adeno-associated virus type 2 (rAAV2) particle assembly using stable producer cell lines,*J. Gene Med.* 6: 555-564 (2004).

Urabe, M. et al., "Insect cells as a factory to produce adeno-associated virus type 2 vectors," *Hum. Gene Ther.* 13: 1925-1943 (2002).

Urlaub, G. et al., "Isolation of Chinese hamster cell mutants deficient in dihydrofolate reductase activity," *Proc. Natl. Acad. Sci. USA*, 77(7): 4216-4220 (1980).

Vandenberghe, L. H. et al., "Efficient serotype-dependent release of functional vector into the culture medium during adeno-associated virus manufacturing," *Hum Gene Ther.*, 21(10): 1251-1257 (2010).

Vincent, K. A. et al., "Replication and packaging of HIV envelope genes in a novel adeno-associated virus vector system," *Vaccines*, Cold Spring Harbor Laboratory Press, 90: 353-359, (1990).

Vincent, K. A. et al., "Analysis of recombinant adeno-associated virus packaging and requirements for rep and cap gene products," *J. Virol.*, 71: 1897-1905 (1997).

Voss, S. D. et al., "The role of enhancers in the regulation of cell-type-specific transcriptional control," *TIBS*, 11: 287-289 (1986).

Wells, J. A. et al. "Cassette mutagenesis: an efficient method for generation of multiple mutations at defended sites," *Gene*, 34: 315-323 (1985).

Xiao, X. et al., "Production of high-titer recombinant adeno-associated virus vectors in the absence of helper adenovirus," *J. Virol.* 72(3):2224-2232 (1998).

Yan, Ziying et al., "Inverted terminal repeat sequences are important for intermolecular recombination and circularization of adeno-associated virus genomes," *Journal of Virology, The American Society for Microbiology, US*, 79(1):364-379 (2005).

Young, J. F. et al., "Adeno-associated Virus—an extreme state of viral defectiveness," *Prog. Med. Virol.*, 25: 113-132 (1979).

Zhao, H., Wolf, T., van der Valk, M., Plewa, C. A., Sheng, J., Lee, K. J., "Cost-Effective and Facile Method of rAAV Production in Suspension-adapted HEK 293 Cells," *Mol. Ther.* 19, Supplement 1:S257, No. 671 (2011).

Zincarelli. C. et al., "Analysis of AAV serotypes 1-9 mediated gene expression and tropism in mice after systemic injection," *Molecular Therapy*, 16: 1073-1080 (2008).

Allay, J. A. et al., "Good manufacturing practice production of self-complementary serotype 8 adeno-associated viral vector for a hemophilia B clinical trial," *Hum Gene Ther.;* 22: 595-604 (2011).

\* cited by examiner pCis-eGFP

The pCis-eGFP vector contains the cDNA encoding enhanced green fluorescence protein (eGFP) flanked by AAV ITRs.

| Feature | |
|---|---|
| ITR: | AAV2 inverted terminal repeat |
| EF1alpha promoter: | elongation factor 1a (EF1a) promoter |
| eGFP: | eGFP gene |
| BGH pA: | bovine growth hormone polyadenylation signal |

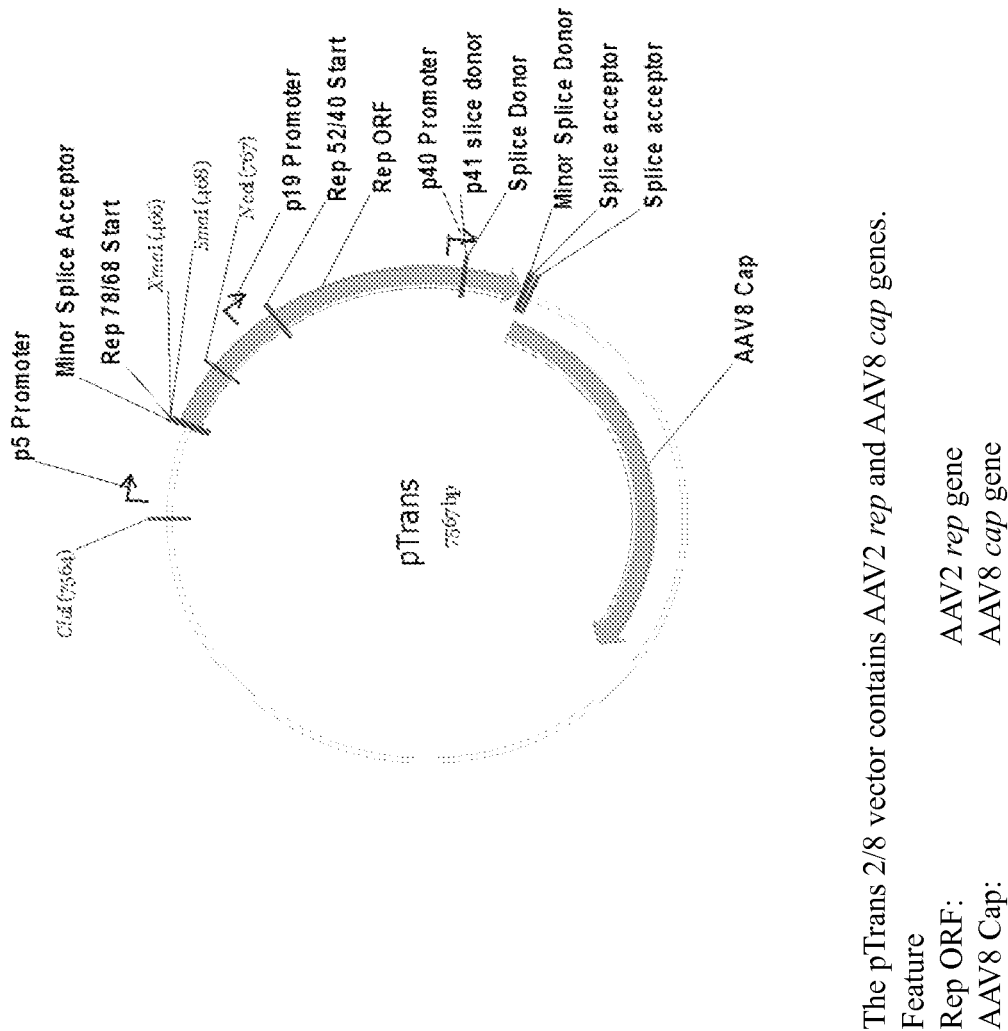

pCis-eGFP

The pCis-eGFP vector contains the cDNA encoding enhanced green fluorescence protein (eGFP) flanked by AAV ITRs.

| Feature | |
|---|---|
| ITR: | AAV2 inverted terminal repeat |
| EF1alpha promoter: | elongation factor 1a (EF1a) promoter |
| eGFP: | eGFP gene |
| WPRE: | the woodchuck hepatitis post-transcriptional regulatory element |
| BGH pA: | bovine growth hormone polyadenylation signal |

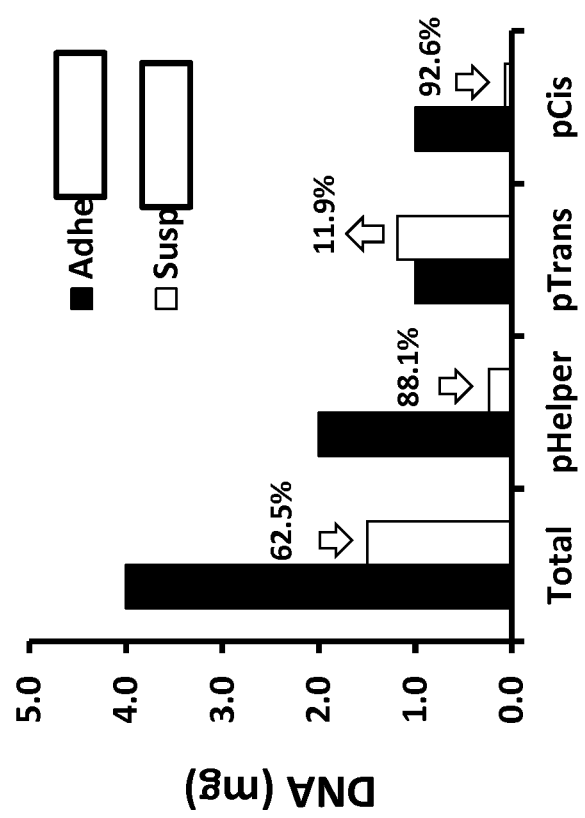

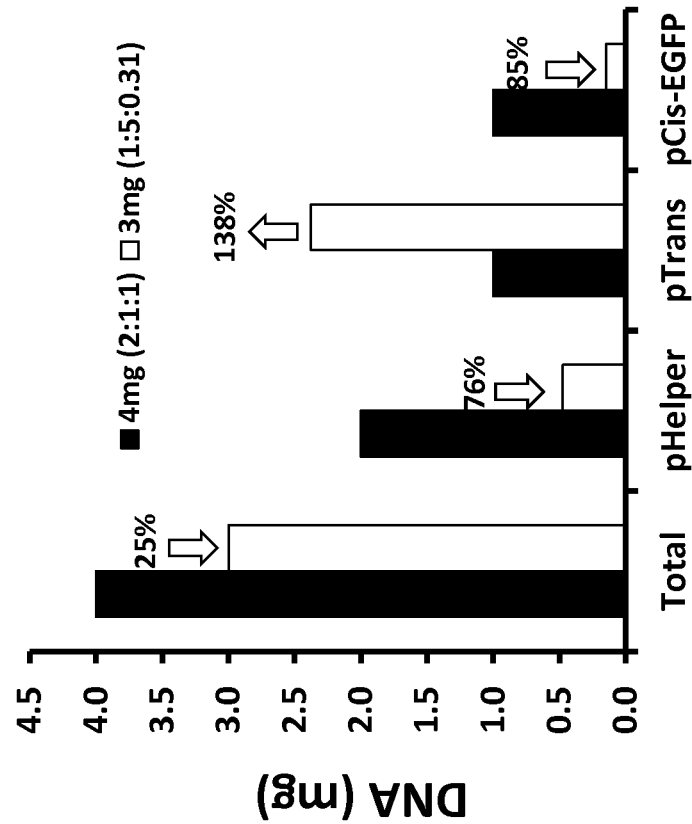
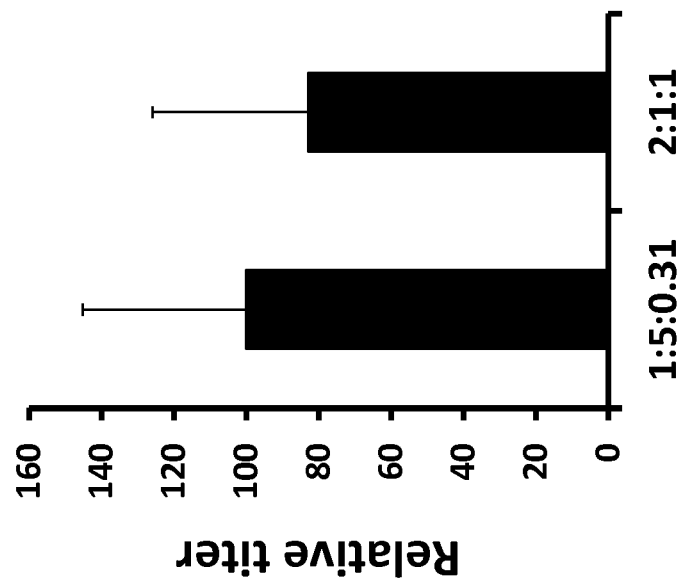
FIG. 4A
FIG. 4B

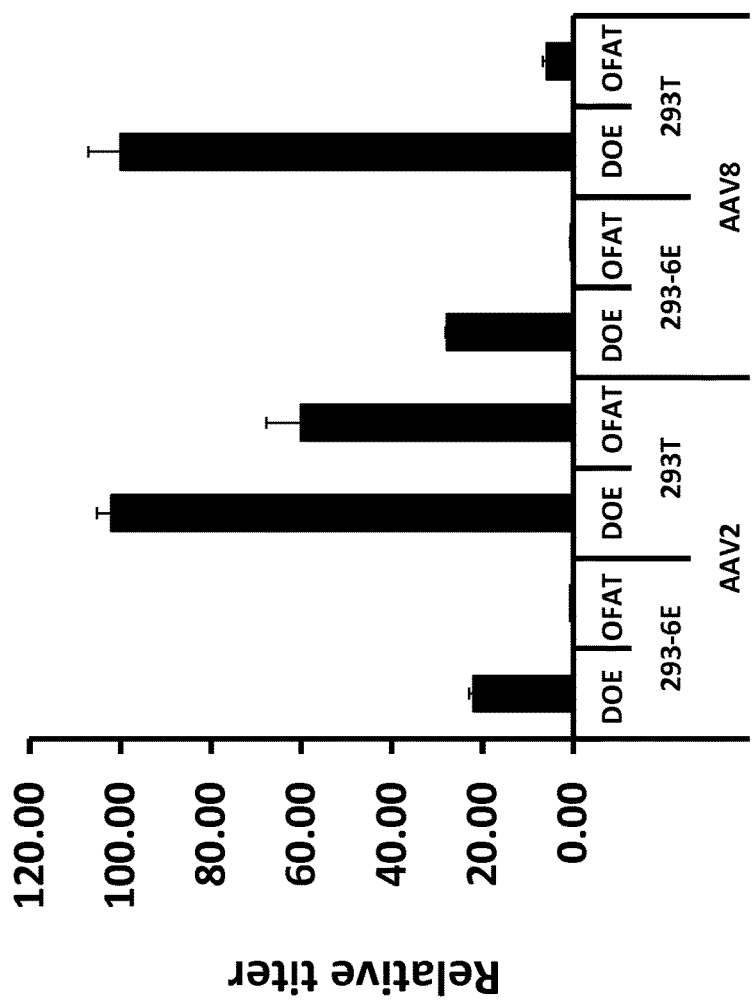
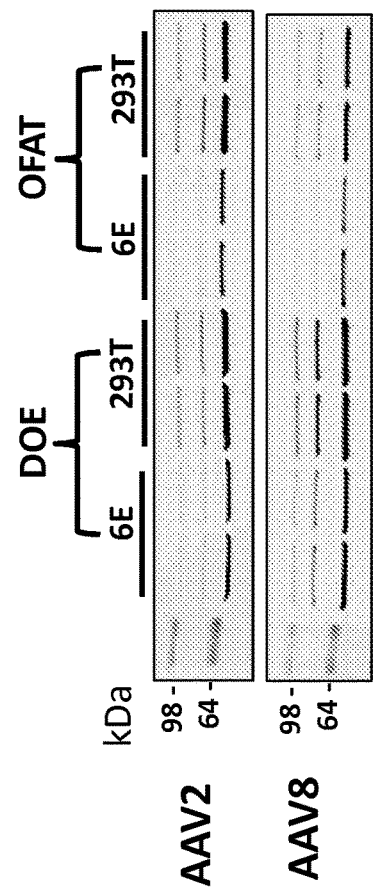
FIG. 9A
FIG. 9B

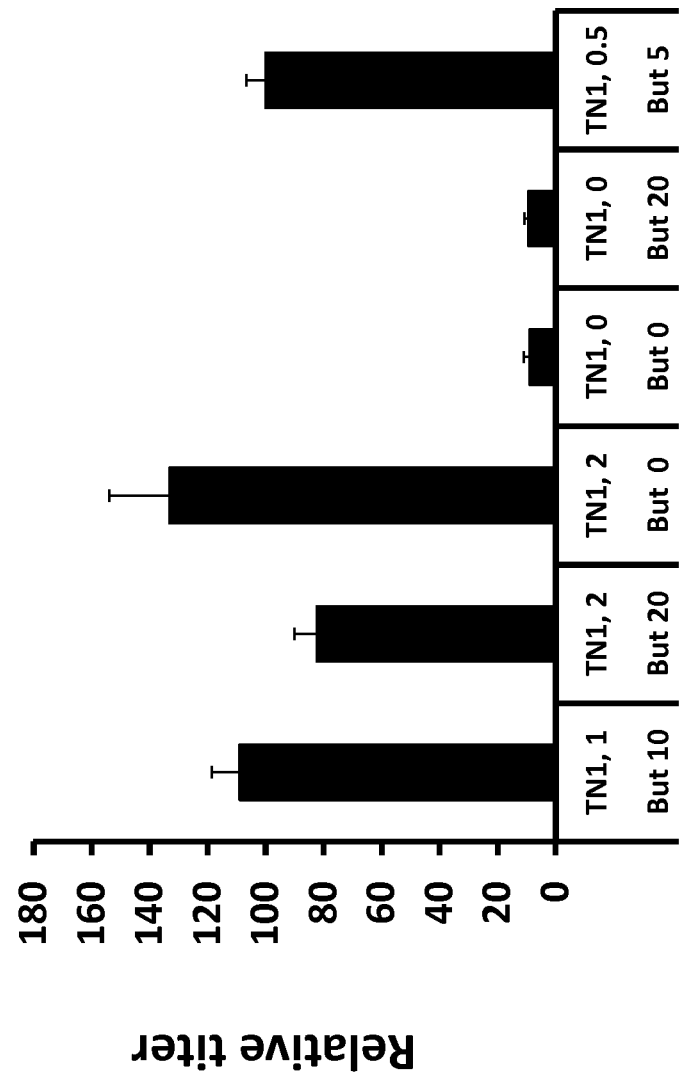

HIGH TITER RECOMBINANT AAV VECTOR PRODUCTION IN ADHERENT AND SUSPENSION CELLS

This application claims the benefit of U.S. Provisional Application No. 61/872,523, filed on Aug. 30, 2013, which is hereby incorporated by reference in its entirety.

The instant application contains a Sequence Listing which has been submitted electronically in ASCII format and is hereby incorporated by reference in its entirety. Said ASCII copy, created on Aug. 28, 2014, is named A-1839-WO-PCT-SeqList082814_ST25.txt and is 2 kilobytes in size.

Throughout this application various publications are referenced within parentheses or brackets. The disclosures of these publications in their entireties are hereby incorporated by reference in this application in order to more fully describe the state of the art to which this invention pertains.

BACKGROUND OF THE INVENTION

1. Field of the Invention

The present invention is directed to the field of recombinant viral vector production.

2. Discussion of the Related Art

Adeno-associated virus (AAV) systems have been used for gene delivery to mammalian cells. AAV is generally considered a good choice for gene delivery because it has not been associated with any human or animal disease and does not appear to alter the biological properties of the host cell upon integration. AAV, which belongs to the genus Dependovirus, is a helper-dependent DNA parvovirus. Thus, in order for effective AAV virion production to occur, the host cell must also be infected with an unrelated helper virus, either adenovirus (Ad), a herpesvirus (HSV), or vaccinia virus. The helper virus supplies accessory functions that are necessary for most steps in AAV replication. In the absence of such infection, AAV establishes a latent state by insertion of its genome into a host cell chromosome. Subsequent infection by a helper virus rescues the integrated copy which can then replicate to produce infectious viral progeny. AAV has a wide host range and is able to replicate in cells from any species so long as there is also a successful infection of such cells with a suitable helper virus. For example, human AAV will replicate in canine cells co-infected with a canine adenovirus. For a review of AAV, see, e.g., Berns & Bohenzky, Advances in Virus Research 32:243-307 (Academic Press, Inc. 1987).

The AAV genome is composed of a linear single-stranded DNA molecule which contains 4681 bases (Berns & Bohenzky, supra). The genome includes inverted terminal repeats (ITRs) at each end which function in cis as origins of DNA replication and as packaging signals for the virus. The ITRs are approximately 145 bp in length. Inverted terminal repeats flank the unique coding nucleotide sequences for the non-structural replication (Rep) proteins and the structural (VP) proteins. The VP proteins (VP1, -2 and -3) form the capsid. The terminal 145 nucleotides are self-complementary and are organized so that an energetically stable intramolecular duplex forming a T-shaped hairpin may be formed. These hairpin structures function as an origin for viral DNA replication, serving as primers for the cellular DNA polymerase complex.

The internal nonrepeated portion of the genome includes two large open reading frames, known as the AAV rep and cap regions, respectively. These regions code for the viral proteins involved in replication and packaging of the virion. In particular, a family of at least four viral proteins are synthesized from the AAV rep region, Rep 78, Rep 68, Rep 52 and Rep 40, named according to their apparent molecular weight. Following wild type AAV infection in mammalian cells the Rep genes (i.e. Rep78 and Rep52) are expressed from the P5 promoter and the P19 promotor, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

The AAV cap region encodes at least three proteins, VP1, VP2 and VP3. For a detailed description of the AAV genome, see, e.g., Muzyczka, Current Topics in Microbiol. and Immunol. 158:97-129 (1992). For descriptions of the construction of recombinant AAV virions see, e.g., U.S. Pat. Nos. 5,173,414 and 5,139,941; International Publication Numbers WO 92/01070 (published 23 Jan. 1992) and WO 93/03769 (published 4 Mar. 1993); Lebkowski et al., Molec. Cell. Biol. 8:3988-3996 (1988); Vincent et al., Vaccines 90 (Cold Spring Harbor Laboratory Press 1990); Carter, Current Opinion in Biotechnology 3:533-539 (1992); Muzyczka, Current Topics in Microbiol. and Immunol. 158:97-129 (1992); Kotin, Human Gene Therapy 5:793-801 (1994).

It is possible to make a mammalian cell line stably expressing AAV rep and AAV cap proteins, but it was also reported that AAV rep protein was toxic to the cells. A majority of rAAV vector production is still done by transient transfection. In addition, transient transfection offers the ease of AAV serotype selection by changing DNA constructs compared to the use of stably transfected cell lines.

Consequently, most ontemporary recombinant AAV (rAAV) virion production involves co-transfection of a host cell with an AAV vector plasmid usually containing one or more transgenes flanked by AAV ITRs, and a construct which provides AAV helper functions (e.g., rep and cap) to complement functions missing from the AAV vector plasmid. In this manner, the host cell is capable of expressing the AAV proteins necessary for AAV replication and packaging. To provide accessory functions, the host cell is then be transfected with a plasmid having accessory function or infected with a helper virus, typically an infectious adenovirus (e.g., type 2 or 5), or herpesvirus.

More particularly, AAV vector plasmids can be engineered to contain a functionally relevant nucleotide sequence of interest (e.g., a selected gene, antisense nucleic acid molecule, ribozyme, or the like) that is flanked by AAV ITRs which provide for AAV replication and packaging functions. After an AAV helper plasmid and an AAV vector plasmid bearing the nucleotide sequence are introduced into the host cell by transient transfection, the accessory function can be provided either by transfecting the cells with a plasmid with accessory genes or by infecting cells with a helper virus, most typically an adenovirus, which, among other functions, transactivates the AAV promoters present on the helper plasmid that direct the transcription and translation of AAV rep and cap regions. Upon subsequent culture of the host cells, rAAV virions (harboring the nucleotide sequence of interest) and helper virus particles are produced.

Adeno-associated virus (AAV) has a stable capsid that is composed of 60 copies of three capsid proteins (VP1, 2 and 3). (Berns K, and Parrish C R, Parvoviridae. in Fields Virology, 5th ed. Ed. by David M. Knipe, Wolters Kluwer/Lippincott Williams & Wilkins, Philadelphia (2007). The commonly used recombinant AAV ("rAAV") vector serotypes are AAV1-9, each with different tissue tropisms. (Zincarelli C, et al., Analysis of AAV serotypes 1-9 mediated gene expression and tropism in mice after systemic injection, Molecular Therapy 16:1073-1080 (2008)).

Recombinant AAV is one of the most promising viral gene transfer vectors because it has high gene transfer efficiency, long-term gene expression, natural replication deficiency, and is non-pathogenic. (Coura R S and Nardi N B., The state of the art of adeno-associated virus-based vectors in gene therapy, Virology J. 4:99-105 (2007)). One of the major challenges for using rAAV vectors has been the difficulty in large scale production of vectors for preclinical target identification/validation studies, or use in large animal models and clinical trials of human gene therapy. (Allay, J A et al., Good manufacturing practice production of self-complementary serotype 8 adeno-associated viral vector for a hemophilia B clinical trial, Hum Gene Ther. 2011; 22:595-604 (2011)). The principle of rAAV vector production is to supply three components to cultured cells: the gene of interest ("GOI") expression cassette flanked by inverted terminal repeats ("ITR"s) of AAV, the rep and cap genes, and trans-acting helper functions. Triple transfection of adherent HEK 293 cells is a commonly used method for rAAV vector production (Xiao, X. and Samulski, R J., Production of high-titer recombinant adeno-associated virus vector in the absence of helper adenovirus, J. Virol. 72:2224-2232 (1998)) and is reported to be efficient (Lock, M. et al, Rapid, simple, and versatile manufacturing of recombinant adeno-associated viral vectors at scale, Hum. Gene Ther. 21:1259-71 (2010)). However, cell culture work involved in rAAV production including expansion, seeding and transfection of adherent HEK 293 cells is cumbersome and resource intensive. Therefore, using cells suspended in aqueous liquid medium ("suspension cells") for rAAV vector production is desirable due to its scalability and cost effectiveness.

Several systems using suspension cells to produce rAAV vectors have been developed and described in the literature:

1. Insect cell (Sf9 or H5 cells)/baculovirus: This system involves infection of insect cells with two recombinant baculoviruses to provide rep, cap and GOI flanked with ITR and has high production efficiency. (Urabe, M. et al., Insect cells as a factory to produce adeno-associated virus type 2 vectors, Hum. Gene Ther. 13:1925-1943 (2002)). Although insect packaging cell lines were recently developed and the number of required baculoviruses was reduced to one, this system still faces several drawbacks, such as long lead time and genomic instability of the baculovirus. (Aslanidi, G. et al., An inducible system for high efficient production of recombinant production of recombinant adeno-associated virus (rAAV) vectors in insect Sf9 cells, Proc. Natl Acad. Sci. USA 106:5059-5064 (2009)).

2. HeLa based cell lines/Ad5 or HSV-1: This approach requires generating a stable rAAV packaging cell line and providing helper functions and transgene cassette using Ad5, or generating a producer cell line and providing helper functions with Ad5 or HSV1. (Gao, G P et al., High-titer adeno-associated viral vectors from a Rep/Cap cell line and hybrid shuttle virus, Hum. Gene Ther. 9:2353-62 (1998); Thorne, B A et al., Manufacturing recombinant adeno-associated viral vectors from producer cell clones, Hum. Gene Ther. 20:707-14 (2009); Toublanc, E. et al., Identification of a replication-defective herpes simplex virus for recombinant adeno-associated virus type 2 (rAAV2) particle assembly using stable producer cell lines, J. Gene Med. 6:555-64 (2004)). The method is suitable for large scale production, but generating stable cell lines is cumbersome and lengthy.

3. BHK21 cells/HSV system: This system utilizes two rHSV-1 vectors to deliver cis and trans factors required for rAAV vector production and has been used for large scale rAAV vector production. (Booth, M J et al., Transfection-free and scalable recombinant AAV vector production using HSV/AAV hybrids, Gene Ther. 11:829-37 (2004)). However, the lengthy time to produce the master viral banks, fragility and pathogenicity/immunogenicity of HSV make this method less favorable.

All of the above methods 1-3 need to ensure the elimination of the virus used from the final rAAV vector preparation.

4. Suspension adapted HEK 293 cells/triple transfection: This is a traditional triple transfection method for rAAV vector production, but in suspension-adapted cells instead of adherent cells. Advantages of this method are scalability, flexibility, simplicity and speed, which are important when different combinations of serotypes and/or GOIs and strict timelines are necessary.

Only a few protocols using suspension-adapted HEK 293 cells/triple transfection have been reported and all were optimized using the one factor at a time (OFAT) method. Park, et al. first explored the possibility of combining suspension HEK 293 cells and polyethyleneimine (PEI) transfection for rAAV2 vector production. (Park, J Y et al., Scalable production adeno-associated virus type 2 vectors via suspension transfection, Biotech. Bioeng. 94:416-430 (2006)). The authors demonstrated that a similar amount of rAAV2 could be generated in suspension cells as compared to adherent cells, and HEK 293T cells were more efficient for rAAV vector production than HEK 293 cells. The cell density ($0.5 \times 10^6$ cells/ml) and the plasmid ratio (1:1:1; pHelper:pTrans:pCis, an equimolar ratio) were not optimized in the study, but the total amount of DNA was optimized to 3 µg/ml. In addition, media changes before and after transfections were required in this protocol.

A more comprehensive study by Durocher, et al. optimized the ratio of the three plasmids (1:1:1 in HEK293E cells), the cell density ($0.5 \times 10^6$ cells/ml, tested densities: 0.5, 1.0 and $2.0 \times 10^6$ cells/ml in HEK293F cells), and harvest time (48 h, to obtain higher infectious virus particles ("IVP") in 293F cells), while the amount of DNA (1 µg/ml) and polyethyleneimine (PEI):DNA (2:1) ratio were kept constant. (Durocher, Y et al., Scalable serum-free production of recombinant adeno-associated virus type 2 by transfection of 293 suspension cells, J. Virol. Methods. 144:32-40 (2007)).

Hildinger, et al. described a more complicated method for rAAV2 production in HEK293E cells. Several media were first tested for rAAV2 and rAAV2/5 vectors production and a 1:1 mixture of RPMI and Ex-Cell was found to be the best production medium. The authors reported that $1 \times 10^6$ cells/ml and 1.25 µg/ml DNA were optimal among the tested conditions. (Hildinger, M et al., High-titer, serum-free production of adeno-associated virus vectors by PEI-mediated plasmid transfection in mammalian suspension cells, Biotechnol. Lett. 29:1713-21 (2007)). The study also demonstrated that increasing capsid protein expression and addition of soy peptones the day after transfection increased rAAV2 vector production yields by approximately 40% and 30%, respectively. This study also showed that higher IVP was obtained when rAAV vectors were harvested 48 hours post-transfection. However, the described method is quite complex, since cells need to be pelleted and re-suspended for splitting, washed before transfection and complemented with an equal volume of Ex-Cell medium 4 hours after transfection. These complex procedures are difficult to apply to large scale production.

Feng, et al. also studied rAAV2 vector production in suspension HEK293 cells with hypothermic treatment. (Feng, L et al., Improvement in the suspension-culture production of recombinant adeno-associated virus-LacZ in HEK-293 cells using PEI-DNA complexes in combination with hypothermic treatment, Biotechnol Appl Biochem. 50:121-32 (2008)). The cytotoxicity of PEI was first explored and the PEI concentration (30 µg/ml) for 80% cell viability was chosen. Based on this data and a gel retardation assay, optimized values for the PEI:DNA ratio (5:1), cell density ($0.5 \times 10^6$ cells/ml), and total DNA (3 µg/ml) were obtained using OFAT-based optimization. The authors showed that transfection efficiency increased after transient hypothermic incubation at 4° C. which arrested cells in G2/M phase. However, the correlation between the increase in transfection efficiency induced by hypothermic treatment and higher rAAV vector production was not shown. It is noteworthy that all of these optimizations used traditional OFAT method for rAAV2 production and resulted in similar optimized values for cell density ($0.5-1 \times 10^6$ cells/ml), and DNA ratio (1:1:1 or 2:1:1, pHelper:pTrans:pCis), although total DNA (1-3 µg/ml) and the PEI:DNA ratios are different between these reports (2:1, 3:1 and 5:1).

The present invention provides a way to produce rAAV virions in cultured mammalian cells, both adherent cells and suspension cells, which is particularly desirable because it can dramatically reduce the input of resources required. These and other benefits the present invention provides.

SUMMARY OF THE INVENTION

The present invention is directed to an in vitro method of producing a recombinant AAV virion in a mammalian host cell (that comprises a functional adenoviral E1A gene, e.g., a HEK 293 cell) and to a rAAV made by the method. The method involves incubating the cell in a transfection medium. The transfection medium can comprise a protein hydrolysate, for example tryptone N1 (TN1). Optionally, the transfection medium contains 0-20 mM sodium butyrate. Included in the transfection medium are also (i) an accessory construct comprising a plasmid (pHelper) comprising adenoviral E2, E4Orf6, and VAI RNA genes operably linked to an origin of replication element and one or more other regulatory sequences; (ii) an AAV helper construct comprising a plasmid (pTrans) comprising AAV rep and AAV cap coding regions operably linked to one or more regulatory sequences; and (iii) a recombinant AAV vector comprising a plasmid (pCis), comprising AAV inverted terminal repeats flanking a heterologous gene of interest operably linked to one or more regulatory sequences. In the inventive method, the ratio of pHelper:pTrans:pCis is 1:1 to 5:0.009 to 0.36 (weight:weight:weight), and preferably 1:1 to 5:0.30 to 0.36 (weight:weight:weight). These plasmid ratios (pHelper:pTrans:pCis, weight:weight:weight) diverge from the widely used 2:1:1, 1:1:1 and 3:1:1 plasmid ratios previously known in the art for production either with cells adherent to a solid substrate or with mammalian cells, such as HEK 293 cells, suspended in an aqueous liquid transfection medium.

One distinct advantage of the inventive method is that it can be employed with adherent HEK 293 cells or HEK 293 cells suspended in an aqueous liquid transfection medium, with a beneficial significant reduction in the total amount of DNA input required compared to previously known methods. Encompassed by the method of producing a recombinant AAV virion in a HEK 293 cell, as described above, are improved parameter values that include higher cell density suspension (e.g., at a cell density of $2.1-3.0 \times 10^6$ cells/mL, preferably $2.2-2.7 \times 10^6$ cells/mL, or more preferably $2.4-2.6 \times 10^6$ cells/mL, or even more preferably about $2.5 \times 10^6$ cells/mL), and/or 1.5 mg/L total DNA, and/or a preferred plasmid ratio of 1:5:0.31 (pHelper:pTrans:pCis, weight: weight:weight). For example, by employing the inventive parameter values, equivalent amounts of genomic copies (GC) of rAAV2/8 vectors were produced in 1 L of suspension HEK293T cells as compared with adherent HEK293T cells in one 10-layer cell culture chamber (e.g., Cell-STACK® 6360 $cm^2$ cell culture chamber; Corning Life Sciences). In addition, the inventive method employed in cell suspension significantly reduced the amount of total DNA, pHelper and pCis-GOI by 62.5%, 88.1% and 92.6%, respectively, compared to another protocol used for adherent HEK293T cells. Moreover, the newly defined plasmid ratio was not uniquely beneficial to suspension production and working examples herein show that the inventive method can also be applied to rAAV2/8 (or other species of hybrid rAAV) vector production in adherent HEK293T cells using $CaPO_4$-mediated transfection. Among the benefits of the inventive method is that it employs substantially lesser amounts of total DNA pHelper and pCis than previously reported methods and OFAT methods. In addition, we also showed that further reduction of the amount of pCis can greatly benefit rAAV production yield, when yields of rAAV vector production for a particular pCis-GOI are much lower than that of average production yields.

BRIEF DESCRIPTION OF THE DRAWINGS

FIG. 1A-F shows generic plasmid maps of pHelper (FIG. 1A), pTrans (in this example for rAAV2/8 hybrid; FIG. 1B), and pCis (in this example with eGFP as the heterologous gene of interest [GOI]; FIG. 1C) plasmids that can be used in the optimization of rAAV vector production in accordance with the invention. FIG. 1D shows a more particular example of a pHelper plasmid; FIG. 1E shows a more particular example of a pTrans plasmid (in this example for rAAV2/8 hybrid); and FIG. 1F shows a more particular example of a pCis plasmid (in this example with eGFP as the heterologous GOI).

In FIG. 2A, Immunoblot analysis of viral capsid proteins in cell lysates. rAAV2/8 vectors carrying various GOIs were generated in either 1 L of suspension HEK293T cells (lanes 1, 3, and 5) using the OFAT-optimized protocol or in adherent HEK293T cells (lanes 2, 4, and 6) in 10-layer cell stacks. FIG. 2B shows relative titers of rAAV2/8-eGFP from one cell stack of adherent cells or 1 L of suspension HEK293T cells using the OFAT-optimized protocol. Suspension, n=1; adherent, n=2.

FIG. 3A-C shows a comparison of rAAV vector production in suspension and adherent HEK 293T cells. FIG. 3A shows relative titers of rAAV2/8-eGFP vectors generated from one liter of suspension HEK293T cells using the DOE-improved protocol (Susp.; n=2) or from adherent HEK293T cells in one cell stack (Adhe; n=2). FIG. 3B shows a comparison of rAAV yields for vectors carrying various GOIs and produced in either 1 L suspension HEK293T cells or adherent HEK293T cells in a 10-layer CellSTACK® cell culture chamber. FIG. 3C shows a comparison of the total amount of DNA and amounts of individual plasmid DNAs used for 1 L of suspension HEK293T cells transfected according to the DOE-improved protocol or for adherent HEK293T cells transfected in one 10-layer CellSTACK® cell culture chamber using the CaPO$_4$-mediated protocol.

FIG. 4A-B shows that the plasmid ratio revealed by DOE in suspension cells (1:5:0.31) also works effectively for adherent HEK293T cells. In FIG. 4A, adherent HEK293T cells in one cell stack were transfected by means of the CaPO$_4$ method using the total amount of DNA and plasmid ratio (pHelper:pTrans:pCis) identified in the DOE optimization (1:5:0.31, left) or the standard reported DNA amount and ratio (2:1:1, right). rAAV2/8 vectors carrying different GOIs (n=6) were purified and the relative titers per Cell-STACK® cell culture chamber are shown. FIG. 4B shows a comparison of the amount of total DNA, pHelper DNA, pTrans DNA, and pCis DNA used for adherent HEK293T cells transfected with either the 1:5:0.31 or 2:1:1 (pHelper:pTrans:pCis-GOI) plasmid ratio.

FIG. 8A and FIG. 8B. rAAV2/8 (A) and rAAV2 (B) production using either AMG2/8 or a commercially obtained Agilent Technologies Inc.'s ("AGL2/8") plasmid set. To compare rAAV2/8 production yields, the AAV2 cap gene in pAAV-RC (AGL) was replaced by the AAV8 cap gene (AGL2/8). The GOI is LacZ for AGL and eGFP for AMG; FIG. 8C shows rAAV2-eGFP vector production using AMG or the published pTrans plasmids pXX2 and pACG2 (Xiao et al. J Virol. 72:2224-32 (1998)). All experiments were carried out using the DOE optimized protocol and with Amgen's pHelper and pCis-eGFP plasmids (FIG. 1A and FIG. 1C). The bars represent the average of duplicates.

FIG. 9A-B shows a comparison of rAAV2 and 2/8 vector production in HEK293-6E and HEK293T cells. The rAAVs were produced in 20-ml suspensions of HEK293T or HEK293-6E cells using DOE-improved or OFAT-optimized protocols (Table 2). In FIG. 9A, the rAAV in the lysate was titered by bDNA assay after purification with AVB Sepharose; FIG. 9B represents an immunoblot of capsid proteins in the lysate. The bars represent the average of duplicates.

FIG. 11A-E illustrates optimization of TN1 and sodium butyrate concentrations with DOE. In FIG. 11A, the DOE-optimization experiments were carried out for rAAV2/8-eGFP production in suspension HEK293T cells. Twenty four hours post transfection, TN1 and sodium butyrate ("But") were added to the culture at the appropriate concentrations. Cells were harvested at 72 hours post-transfection, rAAV2/8-eGFP in cell lysates from each 20-ml culture was purified with AVB Sepharose, and relative titers were determined by bDNA assay; FIG. 11B shows the prediction profiles of effects of TN1 and sodium butyrate on rAAV2/8 vector production. The average optimal concentration was also shown in FIG. 11A; FIG. 11C shows a comparison of the titer yields before and after optimization of the additive concentrations. The rAAV2/8 vectors were produced in 20-ml culture, and TN1 and sodium butyrate ("But") were added 24 hours after transfection at concentrations indicated in the figure. The rAAV2/8 vectors were purified from lysate and GC/ml was determined by bDNA assay. Each bar represents the average of duplicates. The ranges of parameters for experimental design, optimal and 90% of optimal values, and typically used concentrations are shown in Table 5 herein. FIG. 11D shows the comparison of AAV8-empty vector (rAAV2/8 does not carry GOI) production in small (20-mL) and large (1-L) scale. The culture volumes were depicted at the top of the figure. 293T cells were transfected in duplicate according to DOE-optimized condition. Immediately after transfection, 20 ml of culture were removed from the 1-L transfection and cultured in a 125-ml flask (20 ml from 1 L). Different amount of TN1 and sodium butyrate were added to the culture 24 h post transfection, as shown in the figure. The rAAV8-empty vector was then purified with AVB-Sepharose and the capsid proteins were analyzed with silver stain (FIG. 11D), and titer for each sample was determined by bDNA assay (FIG. 11E).

FIG. 12B shows an immunoblot analysis of AAV cap expression. AAV capsid proteins were detected by the method described for FIG. 12A. Molecular weight markers are indicated on the left and dilution factors are indicated on top of the gel. FIG. 12C shows a quantification of rAAV8-Kcnj14 vector yields. The rAAV vectors in the cells and conditioned medium were first purified by using AVB Sepharose, and then the genome copies (GC) of the rAAV vectors were determined by the CyQant fluorescent method (Cell Biolabs, Inc.) and data are presented as the fold-increase of GC (using the DOE-optimized amount as 1). Dilution factors of pCis-Kcnj14 are indicated at the bottom.

DETAILED DESCRIPTION

Figure 1A:
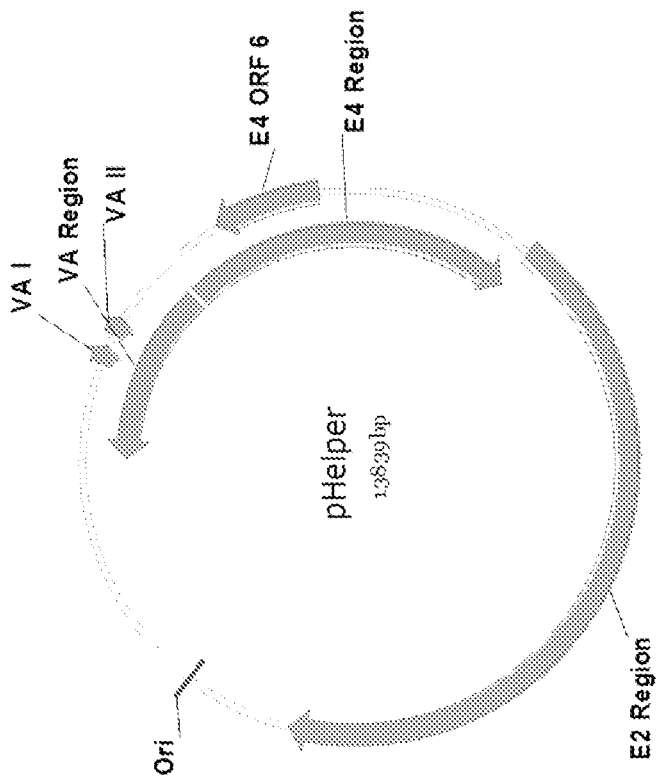
Figure 1B:
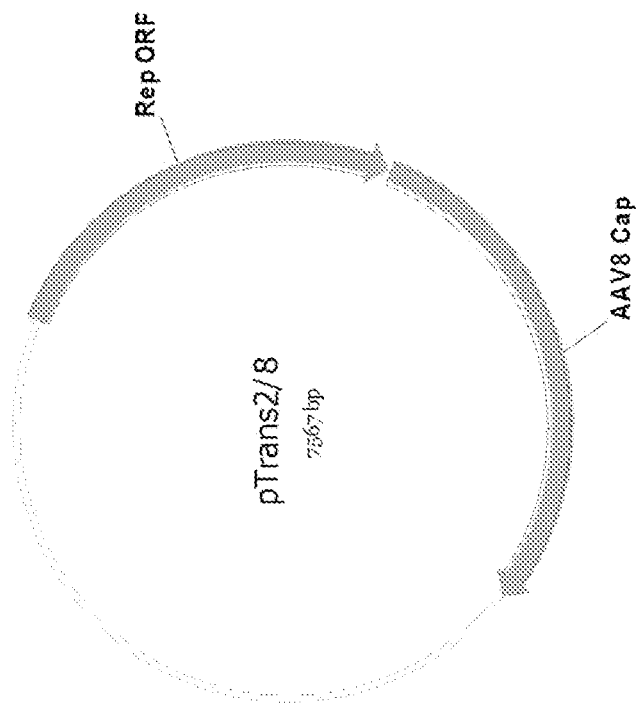
Figure 1C:
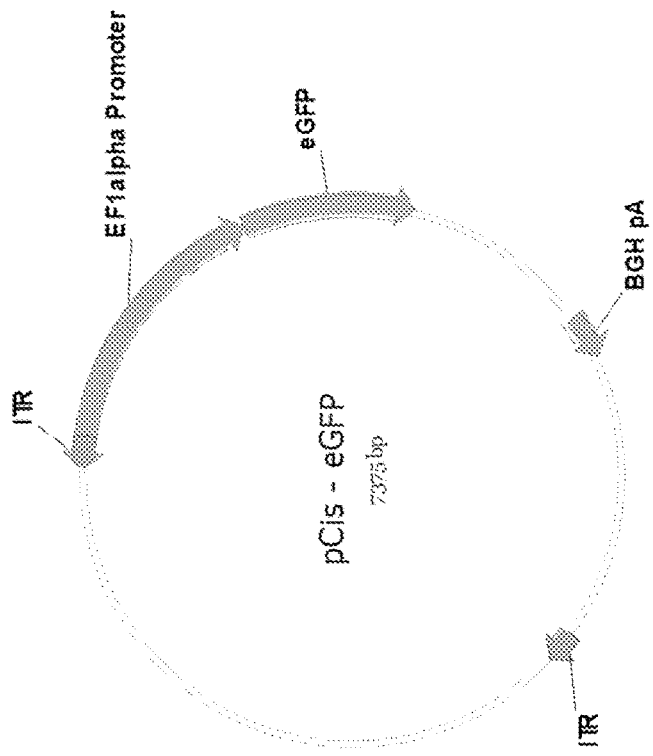
Figure 1D:
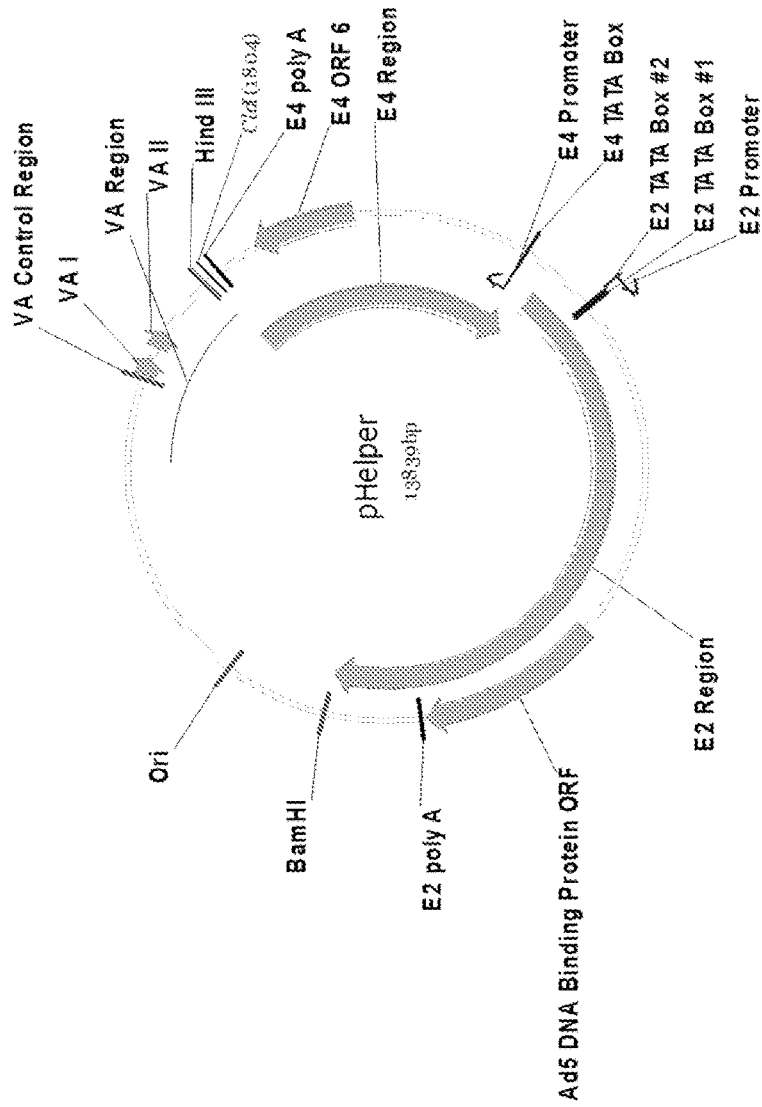
Figure 1F:
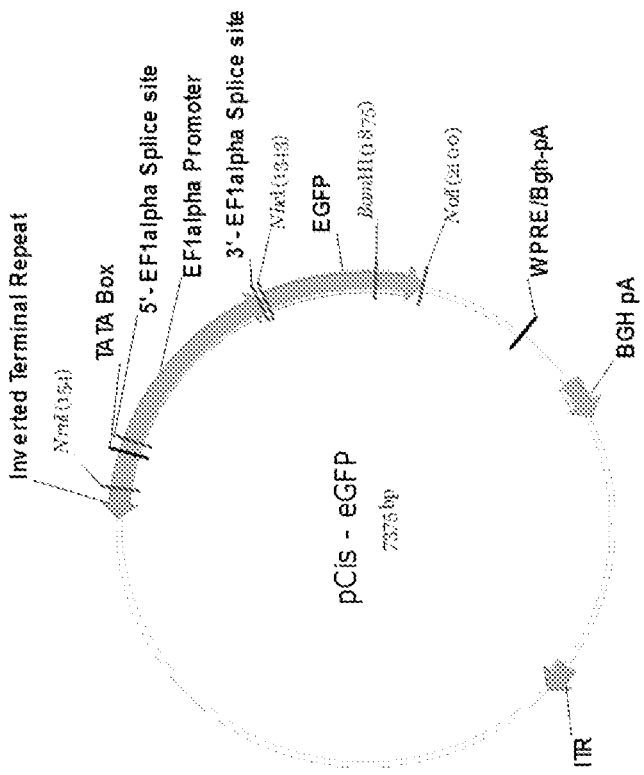

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. A "fusion gene" contains a coding region that encodes a polypeptide or oligopeptide with portions from different proteins that are not naturally found together, or not found naturally together in the same sequence as present in the encoded fusion protein (i.e., a chimeric protein). Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

"Gene transfer" or "gene delivery" refers to methods or systems for inserting foreign DNA into host cells. Gene transfer can result in transient expression of non-integrated transferred DNA, extra chromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

As used herein the term "coding region" or "coding sequence" when used in reference to a structural gene refers to the nucleotide sequences which encode the amino acids found in the nascent polypeptide as a result of translation of an mRNA molecule. A "coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a transcriptional, or translational, as the case may be, stop codon at the 3' (carboxy) terminus.

The coding region is bounded, in eukaryotes, on the 5' side by the nucleotide triplet "ATG" which encodes the initiator methionine and on the 3' side by one of the three triplets which specify stop codons (i.e., TAA, TAG, TGA).

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsulating a heterologous nucleotide sequence of interest that is flanked on both sides by AAV ITRs. A rAAV virion is produced in a suitable host cell, such as but not limited to a HEK 293 cell, comprising an AAV vector, AAV helper functions and accessory functions. In this manner, the host cell is rendered capable of encoding AAV polypeptides that are required for packaging the AAV vector (containing a recombinant nucleotide sequence of interest) into infectious recombinant virion particles for subsequent gene delivery.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vectors, as well as viral vectors.

The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. Nos. 6,022,952 and 6,335,178; Uemura et al., Protein expression vector and utilization thereof, U.S. Pat. No. 7,029,909; Ruben et al., 27 human secreted proteins, US 2003/0104400 A1).

By an "AAV vector" is meant a vector derived from any adeno-associated virus serotype isolated from any animal species, including without limitation, AAV-1, AAV-2, AAV-3, AAV-4, AAV-5, AAV-6, AAV-7, AAV-8 and AAV-9 serotypes, or hybrids of any of these. For example, hybrid AAV vectors are commonly made by employing hybrid trans-complementing constructs that encode rep from AAV2, with cap derived from another serotype displaying the cell tropism of choice, e.g., AAV5.

In this example, the resulting rAAV virion is called rAAV2/5, in which the rep gene is based on recombinant AAV2, i.e., ITRs and rep from AAV2, while the capsid is based on AAV5. Typically, the cell or tissue-tropism displayed by such a hybrid rAAV virion will be the same as for the rAAV serotype that donated the cap, for example, the tropism of a rAAV2/5 hybrid virus should be the same as that of AAV5.

AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

A "recombinant AAV vector" or, interchangeably, "recombinant AAV construct" (rAAV vector) herein refers to a vector comprising one or more heterologous polynucleotide sequences of interest, gene(s) of interest or "transgenes" that are flanked by AAV inverted terminal repeat sequences (ITRs). Such rAAV vectors can be replicated and packaged into infectious viral particles when present in a mammalian or an insect host cell that is expressing AAV rep and cap gene products (i.e. AAV Rep and Cap proteins). When a rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions. A recombinant AAV vector can be in the form of a plasmid ("pCis"), phage, transposon, cosmid, virus, or virion.

By "adeno-associated virus inverted terminal repeats" or "AAV ITRs" is meant the art-recognized regions found at each end of the AAV genome which function together in cis as origins of DNA replication and as packaging signals for the viral genome. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, Human Gene Therapy 5:793-801 (1994); Berns, Parvoviridae and their Replication, in Fundamental Virology (B. N. Fields and D. M. Knipe eds., 2d ed. 1991), for the AAV-2 sequence. As used herein, an "AAV ITR" need not have the wild-type nucleotide sequence depicted in the previously cited references, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV-7, AAV-8, AAV-9, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

By "AAV rep coding region" is meant the art-recognized region of the AAV genome which encodes the replication proteins of the virus which are collectively required to replicate the viral genome and to insert the viral genome into a host genome during latent infection, or functional homologues thereof such as the human herpesvirus 6 (HHV-6) rep gene which is also known to mediate AAV-2 DNA replication. Thomson et al., Virology 204:304-311 (1994). Thus, the rep coding region includes at least the genes encoding for AAV Rep 78 and Rep 68 (the "long forms of Rep"), and Rep 52 and Rep 40 (the "short forms of Rep"), or functional homologues thereof. For a further description of the AAV rep coding region, see e.g., Muzyczka, Current Topics in Microbiol. and Immunol. 158:97-129 (1992); Kotin, Human Gene Therapy 5:793-801 (1994). The rep coding region, as used herein, can be derived from any viral serotype, such as the AAV serotypes described above. The region need not include all of the wild-type genes but may be altered, e.g., by the insertion, deletion or substitution of nucleotides, so long as the rep genes present provide for sufficient integration functions when expressed in a suitable recipient cell.

By "AAV cap coding region" is meant the art-recognized region of the AAV genome which encodes the coat proteins of the virus which are collectively required for packaging the viral genome. Thus, the cap coding region includes at least the genes encoding for the coat proteins VP1, VP2 and VP3. For a further description of the cap coding region, see, e.g., Muzyczka, Current Topics in Microbiol. and Immunol. 158:97-129 (1992); Kotin, Human Gene Therapy 5:793-801 (1994). The AAV cap coding region, as used herein, can be derived from any AAV serotype, as described above. The region need not include all of the wild-type cap genes but may be altered, e.g., by the insertion, deletion or substitution of nucleotides, so long as the genes provide for sufficient packaging functions when present in a host cell along with an AAV vector.

"AAV helper functions" refer to AAV-derived coding sequences which can be expressed to provide AAV gene products that, in turn, function in trans for productive AAV replication. Thus, AAV helper functions include the rep and cap coding regions. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refer to a nucleic acid molecule that includes nucleotide sequences providing AAV helper functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for AAV replication; however, helper constructs lack AAV ITRs and can neither replicate nor package themselves. AAV helper constructs can be in the form of a plasmid ("pTrans"), phage, transposon, cosmid, virus, or virion. A number of AAV helper constructs have been described, such as the commonly used plasmids pAAV/Ad and pIM29+45 which encode both Rep and Cap expression products. See, e.g., Samulski et al., J. Virol. 63:3822-3828 (1989); McCarty et al., J. Virol. 65:2936-2945 (1991). A number of other vectors have described which encode Rep and/or Cap expression products. See, e.g., U.S. Pat. No. 5,139,941.

The term "accessory functions" refers to non-AAV derived viral and/or cellular functions upon which AAV is dependent for its replication. Thus, the term encompasses proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus and vaccinia virus. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles.

For example, adenovirus-derived accessory functions have been widely studied, and a number or adenovirus genes involved in accessory functions have been identified and partially characterized. See, e.g., Carter, Adeno-Associated Virus Helper Functions, in I CRC Handbook of Parvoviruses (P. Tijssen ed., 1990); Muzyczka, Curr. Topics. Microbiol and Immun 158:97-129 (1992). Specifically, early adenoviral gene regions E1A (present, for example, in HEK 293 cells), E2A, E4Orf6, VAI RNA, and optionally VAII RNA, and, optionally, E1B (also present in HEK 293 cells) are thought to participate in the accessory process. Janik et al., Proc. Natl. Acad. Sci. USA 78:1925-1929 (1981). Herpesvirus-derived accessory functions have been described. See, e.g., Young et al., Prog. Med. Virol. 25:113 (1979). Vaccinia virus-derived accessory functions have also been described. See, e.g., Carter (1990), supra; Schlehofer et al., Virology 152:110-117 (1986).

It has been demonstrated that the full-complement of adenovirus genes are not required for accessory functions. In particular, adenovirus mutants incapable of DNA replication and late gene synthesis have been shown to be permissive for AAV replication. Ito et al., J. Gen. Virol. 9:243 (1970); Ishibashi et al, Virology 45:317 (1971). Similarly, mutants within the E2B and E3 regions have been shown to support AAV replication, indicating that the E2B and E3 regions are probably not involved in providing accessory functions. Carter et al., Virology 126:505 (1983). However, adenoviruses defective in the E1 region, or having a deleted E4 region, are unable to support AAV replication. Thus, E1A and E4 regions are likely required for AAV replication, either directly or indirectly. Laughlin et al., J. Virol 41:868 (1982); Janik et al., Proc. Natl. Acad. Sci. USA 78:1925 (1981); Carter et al., Virology 126:505 (1983). Other characterized Ad mutants include: E1B (Laughlin et al. (1982), supra; Janik et al. (1981), supra; Ostrove et al., Virology 104:502) (1980); E2A (Handa et al., J. Gen. Virol. 29:239 (1975); Strauss et al., J. Virol. 17:140 (1976); Myers et al., J. Virol. 35:665 (1980); Jay et al., Proc. Natl. Acad. Sci. USA 78:2927 (1981); Myers et al., J. Biol. Chem. 256:567 (1981)); E2B (Carter, Adeno-Associated Virus Helper Functions, in I CRC Handbook of Parvoviruses (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., J. Virol. 62:206-210 (1988), recently reported that E1B55k is required for AAV virion production, while E1B19k is not. In addition, International Publication WO 97/17458 and Matshushita et al., Gene Therapy 5:938-945 (1998), describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797. The term "accessory construct" or, interchangeably, "accessory function vector," refers to a nucleic acid molecule that includes nucleotide sequences providing accessory functions. An accessory construct can be in the form of a plasmid ("pHelper"), phage, transposon, cosmid, virus, or virion.

By "capable of supporting efficient rAAV virion production" is meant the ability of an accessory function vector or system to provide accessory functions that are sufficient to complement rAAV virion productions in a particular host cell at a level substantially equivalent to or greater than that which could be obtained upon infection of the host cell with an adenovirus helper virus. Thus, the ability of an accessory function vector or system to support efficient rAAV virion production can be determined by comparing rAAV virion titers obtained using the accessory vector or system with titers obtained using infection with an infectious adenovirus. More particularly, an accessory function vector or system supports efficient rAAV virion production substantially equivalent to, or greater than, that obtained using an infectious adenovirus when the amount of virions obtained from an equivalent number of host cells is not more than about 200 fold less than the amount obtained using adenovirus infection, more preferably not more than about 100 fold less, and most preferable equal to, or greater than, the amount obtained using adenovirus infection.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs and vectors that encode Rep and/or Cap expression products have been described. See, e.g., U.S. Pat. Nos. 6,001,650, 5,139,941, 6,376,237, 8,007,780, all incorporated herein by reference in their entireties; Samulski et al. J. Virol. 63:3822-3828 (1989); and McCarty et al. J. Virol. 65:2936-2945 (1991).

"Mammal" refers to any animal classified as a mammal, including humans, domestic and farm animals, and zoo, sports, or pet animals, such as dogs, horses, cats, cows, rodents (e.g., rats, mice, guinea pigs, hamsters), rabbits, pigs, sheep, goats, primates (e.g., monkeys, apes), etc. A "non-human" mammal is a mammal other than a human. The term "progeny" refers to any and all future generations derived and descending from a particular cell or mammal.

"Non-human primate" or "NHP" means any non-human member of the order Primates, which contains prosimians (including lemurs, lorises, galagos and tarsiers) and, preferably simians (monkeys and apes), for example, baboons (*Papio* spp.), African green monkeys (*Chlorocebus* spp.), macaques (e.g., rhesus monkeys (*Macaca mulatta*), cynomolgus monkeys (*Macaca fascicularis*)), spider monkeys (*Ateles* spp.), chimpanzees and bonobos (*Pan* spp.), gorillas (*Gorilla* spp.), gibbons (Hylobatidae), and orangutans (*Pongo* spp.). As noted, cynomolgus monkeys (also known as "cynos", in singular "cyno") are macaques (*Macaca fascicularis* synonym *M. cynomolgus*).

The term "transfection" is used to refer to the uptake of foreign or heterologous DNA by a cell, and a cell has been "transfected" when exogenous DNA has been introduced inside the cell membrane. A number of transfection techniques are generally known in the art. See, e.g., Graham et al. (1973) Virology, 52: 456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a nucleotide integration vector and other nucleic acid molecules, into suitable host cells. Cells to be transfected are surrounded by an aqueous "transfection medium" suitable for the transfection method employed. In some cases, the transfection medium can be a culture medium. The transfection medium can contain about 0.1-2% (w/v) protein hydrolysate, or yeastolate, such as but not limited to a peptone (e.g., tryptone [TN1]). (See, e.g., Pham et al., Transient gene expression in HEK293 cells: peptone addition post-transfection improves recombinant protein synthesis, Biotechnol. & Bioeng. 90(3):332-44 (2005)). Within the inventive method, it can be useful in small-scale transfection cultures (e.g., 20-mL), to include tryptone N1 (TN1) in the transfection medium at a concentration of 1.4-1.6% (w/v), and preferably 1.475-1.525% (w/v), and more preferably 1.50% (w/v)), and sodium butyrate can be added, optionally, at a concentration of 0-20 mM. However, in large scale (e.g., 1-L) batches, 0.5% (w/v) protein hydrolysate and 5 mM sodium butyrate increased yield of rAAV virions.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-358, National Biomedical Research Foundation, Washington, D.C., which adapts the local homology algorithm of Smith and Waterman Advances in Appl. Math. 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

The term "heterologous" as it relates to nucleic acid sequences such as coding sequences and control sequences, denotes sequences that are not in nature normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct that is not normally present in the cell would be considered heterologous for purposes of this invention. Allelic variation or naturally occurring mutational events do not give rise to heterologous DNA, as used herein.

A "heterologous gene of interest" (GOI), or interchangeably "transgene" or interchangeably "heterologous nucleic acid" (HNA), is any desired gene that can be incorporated into a rAVV virion, which has a packaging capacity of about 5.3 kb (Joshua et al., J. Virol., 79: 9933-9944, 2005), publication described that genome 5.3 kb and higher showed inefficient packaging efficiency, within a log). The transgene optionally may be operably linked to other genetic elements (such as a promoter, poly A sequence and the like) that may serve to modulate, either directly, or indirectly in conjunction with the cellular machinery, the transcription and/or expression of the transgene. Alternatively or additionally, the transgene may be linked to nucleotide sequences that aid in integration of the transgene into the chromosomal DNA of the mammalian cell nucleus (as for example, in homologous recombination). The transgene may be comprised of a nucleotide sequence that is either homologous or heterologous to a particular nucleotide sequence in the mammal's endogenous genetic material, or is a hybrid sequence (i.e. one or more portions of the transgene are homologous, and one or more portions are heterologous to the mammal's genetic material). The transgene nucleotide sequence may encode a polypeptide or a variant of a polypeptide, found endogenously in the mammalian host cell, it may encode a polypeptide not naturally occurring in the mammalian cell (i.e. an exogenous polypeptide), or it may encode a hybrid of endogenous and exogenous polypeptides. Where the transgene is operably linked to a promoter, the promoter may be homologous or heterologous to the mammalian cell and/or to the transgene. Alternatively, the promoter may be a hybrid of endogenous and exogenous promoter elements (enhancers, silencers, suppressors, and the like).

For example, the GOI or transgene can be a readily detectable and/or assayable marker gene, such as a fluorescent protein gene (e.g., green fluorescent protein (GFP) gene, phycobiliprotein gene), luciferase gene, or antibody resistance gene, which can be incorporated into the expression construct whose expression or presence in the genome can easily be detected. The marker gene is usually operably linked to its own promoter or to another strong promoter from any source that will be active or can easily be activated in the cell into which it is inserted; however, the marker gene need not have its own promoter attached as it may be transcribed using the promoter of the gene of interest to be expressed (or suppressed, in the case of a knock-out construct carrying a shRNA expression cassette). In addition, the marker gene will normally have a polyA sequence attached to the 3' end of the gene; this sequence serves to terminate transcription of the gene. Preferred marker genes are luciferase, beta-gal (beta-galactosidase), an alkaline phophatase (e.g., human placental secreted alkaline phosphatase [SEAP]), or any antibiotic resistance gene such as neo (the neomycin resistance gene). The term "knockout construct" refers to a nucleic acid sequence that is designed to decrease or suppress expression of a protein encoded by endogenous DNA sequences in a cell (Khan et al., Nat Protoc. 6:482-501 (2011) and Miller D G., Methods Mol Biol. 807:301-15 (2011)). The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout can also be achieved through highly conserved cellular phenomenon RNA interference (RNAi)—the sequence-specific post-transcriptional silencing of gene expression mediated by small double-stranded RNAs (Grimm et al., Hematology Am Soc Hematol Educ Program. 2007:473-81, Nizzardo et al., Cell Mol Life Sci. 69:1641-50, 2012, and Miyazaki et al., Nat Med. 18:1136-41. 2012). The knockout construct is typically composed of (1) RNA polymerase III [pol III] promoter, typically H1 or U6 promoters, to drive transcription of small RNA, (2) a nucleic acid sequence to encode small hairpin RNA ([shRNA], form a double-stranded RNA via hairpin) and (3) a transcription termination signal for RNA pol III. The knockout construct is inserted into a cell, shRNA is transcribed and processed by cellular phenomenon to achieve knockout via posttranscriptional level, typically lead to RNA of GOI degradation and/or inefficient translation of GOI. The knockout construct nucleic acid sequence may comprise 1) a full or partial sequence of one or more exons and/or introns of the gene to be suppressed, 2) a full or partial promoter sequence of the gene to be suppressed, or 3) combinations thereof (See, e.g., Khan, I F et al., AAV-mediated gene targeting methods for human cells, Nat Protoc. 6:482-501 (2011).; Miller, D G, AAV-mediated gene targeting, Methods Mol Biol. 807:301-15 (2011).; Grimm, D et al., RNAi and gene therapy: a mutual attraction, Hematology Am Soc Hematol Educ Program. 2007:473-81; Nizzardo, M et al., Review: Research advances in gene therapy approaches for the treatment of amyotrophic lateral sclerosis, Cell Mol Life Sci. 69:1641-50 (2012)).

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. Such modified forms include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotide residues. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including an isotopic label (e.g., $^{125}$I, $^{14}$C, $^{13}$C, $^{35}$S, $^{3}$H, $^{2}$H, $^{13}$N, $^{15}$N, $^{18}$O, $^{17}$O, etc.), for ease of quantification or detection, a fluorescent label, a hapten or an antigenic label, for detection assays. Oligonucleotides may be used, for example, as PCR primers, cloning primers or hybridization probes.

A "polynucleotide sequence" or "nucleotide sequence" or "nucleic acid sequence," as used interchangeably herein, is the primary sequence of nucleotide residues in a polynucleotide, including of an oligonucleotide, a DNA, a RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences." A "nucleic acid" sequence captures sequences that include any of the known base analogues of DNA and RNA such as, but not limited to 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term "control sequence" or "control signal", or interchangeably, "regulatory sequence", refers to a polynucleotide sequence that can, in a particular host cell, affect the expression and processing of coding sequences. The nature of such control sequences may depend upon the host organism. In particular embodiments, control sequences for prokaryotes may include a promoter, a ribosomal binding site, and a transcription termination sequence. Control sequences for eukaryotes may include promoters comprising one or a plurality of recognition sites for transcription factors, polyadenylation signals, transcription termination sequences, upstream regulatory domains, origins of replication, internal ribosome entry sites ("IRES"), transcription enhancer sequences or elements, and the like, which collectively provide for the replication, transcription and translation of a coding sequence in a recipient cell, polyadenylation sites, and transcription termination sequences. Not all of these control sequences need always be present so long as the selected coding sequence is capable of being replicated, transcribed and translated in an appropriate host cell. Control sequences can include leader sequences and/or fusion partner sequences. Promoters and enhancers consist of short arrays of DNA that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986) and Maniatis, et al., Science 236:1237 (1987)).

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of nucleic acid elements wherein the components so described are configured so as to perform their usual function. Nucleic acid sequences are "operably linked" in such a manner that a nucleic acid molecule capable of directing the transcription of a given gene and/or the synthesis of a desired protein molecule is produced. The term also refers to the linkage of amino acid sequences in such a manner so that a functional protein is produced. For example, a control sequence in a vector that is "operably linked" to a protein coding sequence is ligated thereto so that expression of the protein coding sequence is achieved under conditions compatible with the transcriptional activity of the control sequences. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express a polypeptide (e.g., an oligopeptide or antibody) where, for example, the nucleic acid molecule is in a chromosomal location different from that of natural cells. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "5 prime (5')" or "3 prime (3')" relative to another sequence, it is to be understood that it is the position of the sequences in the "sense" or "coding" strand of a DNA molecule that is being referred to as is conventional in the art.

A "functional homologue," or a "functional equivalent" of a given AAV polypeptide includes molecules derived from the native polypeptide sequence, as well as recombinantly produced or chemically synthesized polypeptides which function in a manner similar to the reference AAV molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

By "capable of efficient transduction" is meant that the mutated constructs of the invention provide for rAAV vectors or virions that retain the ability to transfect cells in vitro and/or in vivo at a level that is within 1-10% of the transfection efficiency obtained using the corresponding wild-type sequence. Preferably, the mutant retains the ability to transfect cells or tissues at a level that is within 10-100% of the corresponding wild-type sequence. The mutated sequence may even provide for a construct with enhanced ability to transfect cells and tissues. Transduction efficiency is readily determined using techniques well known in the art, including the in vitro transduction assay described in the Examples.

As used herein, the terms "cell culture medium" and "culture medium" refer to a nutrient solution used for growing mammalian cells in vitro that typically provides at least one component from one or more of the following categories: 1) an energy source, usually in the form of a carbohydrate such as, for example, glucose; 2) one or more of all essential amino acids, and usually the basic set of twenty amino acids plus cysteine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The nutrient solution may optionally be supplemented with additional components to optimize growth and/or transfection of cells.

The mammalian cell culture within the present invention is prepared in a medium suitable for the particular cell being cultured. Suitable cell culture media that may be used for culturing a particular cell type would be apparent to one of ordinary skill in the art. Exemplary commercially available media include, for example, Ham's F10 (SIGMA), Minimal Essential Medium (MEM, SIGMA), RPMI-1640 (SIGMA), Dulbecco's Modified Eagle's Medium (DMEM, SIGMA); Iscove modified Dulbecco medium (Gibco) containing 10% fetal bovine serum (see, Xiao et al., Production of High-Titer Recombinant Adeno-Associated Virus Vectors in the Absence of Helper Adenovirus, J Virol., 72: 2224-2232 (1998)), and DMEM/F12 (Life Technologies). Any of these or other suitable media may be supplemented as necessary with hormones and/or other growth factors (such as but not limited to insulin, transferrin, or epidermal growth factor), salts (such as sodium chloride, calcium, magnesium, and phosphate), buffers (such as HEPES), nucleosides (such as adenosine and thymidine), antibiotics (such as puromycin, neomycin, hygromycin, blasticidin, or Gentamycin™), trace elements (defined as inorganic compounds usually present at final concentrations in the micromolar range) lipids (such as linoleic or other fatty acids) and their suitable carriers, and glucose or an equivalent energy source, and/or modified as described herein to facilitate production of recombinant glycoproteins having low-mannose content. In a particular embodiment, the cell culture medium is serum-free.

When defined medium that is serum-free and/or free of protein hydrolysate (e.g., peptone-free) is used, the medium is usually enriched for particular amino acids, vitamins and/or trace elements (see, for example, U.S. Pat. No. 5,122,469 to Mather et al., and U.S. Pat. No. 5,633,162 to Keen et al.). Depending upon the requirements of the particular cell line used or method, culture medium can contain a serum additive such as Fetal Bovine Serum, or a serum replacement. Examples of serum-replacements (for serum-free growth of cells) are TCH™, TM-235™, and TCH™; these products are available commercially from Celox (St. Paul, Minn.), and KOSR (knockout (KO) serum replacement; Life Technologies).

In the methods and compositions of the invention, cells can be grown in serum-free, protein-free, growth factor-free, and/or peptone-free media. The term "serum-free" as applied to media in general includes any mammalian cell culture medium that does not contain serum, such as fetal bovine serum (FBS). The term "insulin-free" as applied to media includes any medium to which no exogenous insulin has been added. By exogenous is meant, in this context, other than that produced by the culturing of the cells themselves. The term "growth-factor free" as applied to media includes any medium to which no exogenous growth factor (e.g., insulin, IGF-1) has been added. The term "peptone-free" as applied to media includes any medium to which no exogenous protein hydrolysates have been added such as, for example, animal and/or plant protein hydrolysates.

Optimally, for purposes of the present invention, the culture medium used is serum-free, or essentially serum-free unless serum is required by the inventive methods or for the growth or maintenance of a particular cell type or cell line. By "serum-free", it is understood that the concentration of serum in the medium is preferably less than 0.1% (v/v) serum and more preferably less than 0.01% (v/v) serum. By "essentially serum-free" is meant that less than about 2% (v/v) serum is present, more preferably less than about 1% (v/v) serum is present, still more preferably less than about 0.5% (v/v) serum is present, yet still more preferably less than about 0.1% (v/v) serum is present.

"Culturing" or "incubating" (used interchangeably with respect to the growth, transformation and/or maintenance of cells or cell lines) is under conditions of sterility, temperature, pH, atmospheric gas content (e.g., oxygen, carbon dioxide, dinitrogen), humidity, culture container, culture volume, passaging, motion, and other parameters suitable for the intended purpose and conventionally known in the art of mammalian cell culture.

"Polypeptide" and "protein", or "proteinaceous molecule" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, fusion proteins can be derivatized as described herein by well-known organic chemistry techniques. The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "domain" or "region" (used interchangeably herein) of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

The term "antibody" is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', F(ab')$_2$, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes typically have antibody-dependent cellular cytotoxicity (ADCC) activity. Glycosylated and unglycosylated antibodies are included within the term "antibody".

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. A "mammalian host cell" is a cell originally derived from a mammal or is a progeny cell thereof.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

Production of AAV Vectors.

Recombinant AAV virions may be produced using a variety of techniques known in the art, including the triple transfection method (described in detail in U.S. Pat. No. 6,001,650, the entirety of which is incorporated herein by reference). This system involves the use of three vectors for rAAV virion production, including an AAV helper function vector, an accessory function vector, and a rAAV vector that contains the HNA. One of skill in the art will appreciate, however, that the nucleic acid sequences encoded by these vectors can be provided on two or more vectors in various combinations.

The AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Examples of vectors suitable for use with the present invention include pHLP19, described in U.S. Pat. No. 6,001,650 and pRep6cap6 vector, described in U.S. Pat. No. 6,156,303, the disclosure of which is hereby incorporated by reference in its entirety.

The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus. In a preferred embodiment, the accessory function plasmid pladeno5 is used (details regarding pLadeno5 are described in U.S. Pat. No. 6,004,797, the disclosure of which is hereby incorporated by reference in its entirety). This plasmid provides a complete set of adenovirus accessory functions for AAV vector production, but lacks the components necessary to form replication-competent adenovirus.

The rAAV vector containing the heterologous gene of interest (GOI), or nucleic acid (HNA), may be constructed using ITRs from any of the various AAV serotypes. The RNA comprises nucleic acid sequences joined together that are otherwise not found together in nature. To illustrate the point, an example of an HNA is a gene flanked by nucleotide sequences not found in association with that gene in nature. Another example of an HNA is a gene that itself is not found in nature (e.g., synthetic sequences having codons different from the native gene). Allelic variation or naturally occurring mutational events do not give rise to HNAs, as used herein. An HNA can comprise an anti-sense RNA molecule, a ribozyme, or a gene encoding a polypeptide.

The HNA is operably linked to a heterologous promoter (constitutive, cell-specific, or inducible) such that the HNA is capable of being expressed in the ultimate target cells to be transduced by the rAAV virion (e.g., neurons, lung cells, or liver cells) under appropriate or desirable conditions. Numerous examples of constitutive, cell-specific, and inducible promoters are known in the art, and one of skill could readily select a promoter for a specific intended use, e.g., the selection of the constitutive CMV promoter for strong levels of continuous or near-continuous expression, or the selection of the inducible ecdysone promoter for induced expression. Induced expression allows the skilled artisan to control the amount of protein that is synthesized. In this manner, it is possible to vary the concentration of a protein product expressed in a rAAV-transduced mammalian cell, or in a non-human mammal or human patient who may ultimately receive the rAAV virion in gene therapy. Other examples of well known inducible promoters are: steroid promoters (e.g., estrogen and androgen promoters) and metallothionein promoters.

Selection of a Heterologous Gene(s) of Interest (GOI).

Typically, the GOI(s) or transgene(s) useful in the present invention will be a nucleotide sequence encoding a polypeptide of interest, e.g., a polypeptide involved in the nervous system, an immune response, hematopoiesis, inflammation, cell growth and proliferation, cell lineage differentiation, and/or the stress response. The polypeptide can be an enzyme, ion channel, receptor (e.g., a GPCR), hormone, cytokine, chemokine, or an antibody or antibody fragment. Included within the scope of this invention is the insertion of one, two, or more transgenes into the rAAV virion.

Where more than one transgene is used in this invention, the transgenes may be prepared and inserted individually, or may be generated together as one construct for insertion. The transgenes may be homologous or heterologous to both the promoter selected to drive expression of each transgene and/or to the mammal or mammalian cell type ultimately intended to be administered the rAAV virion. Further, the transgene may be a full length cDNA or genomic DNA sequence, or any fragment, subunit or mutant thereof that has at least some biological activity i.e., exhibits an effect at any level (biochemical, cellular and/or morphological) that is not readily observed in a wild type, non-transgenic mammal or mammalian cell type of the same species. Optionally, the transgene may be a hybrid nucleotide sequence, i.e., one constructed from homologous and/or heterologous cDNA and/or genomic DNA fragments. The transgene may also optionally be a mutant of one or more naturally occurring cDNA and/or genomic sequences, or an allelic variant thereof.

Each transgene may be isolated and obtained in suitable quantity using one or more methods that are well known in the art. These methods and others useful for isolating a transgene are set forth, for example, in Sambrook et al. (Molecular Cloning: A Laboratory Manual, Cold Spring Harbor Laboratory Press, Cold Spring Harbor, N.Y. [1989]) and in Berger and Kimmel (Methods in Enzymology: Guide to Molecular Cloning Techniques, vol. 152, Academic Press, Inc., San Diego, Calif. (1987)).

Where the nucleotide sequence of each transgene is known, the transgene may be synthesized, in whole or in part, using chemical synthesis methods such as those described in Engels et al. (Angew. Chem. Int. Ed. Engl., 28:716-734 [1989]). These methods include, inter alia, the phosphotriester, phosphoramidite and H-phosphonate methods of nucleic acid synthesis. Alternatively, the transgene may be obtained by screening an appropriate cDNA or genomic library using one or more nucleic acid probes (oligonucleotides, cDNA or genomic DNA fragments with an acceptable level of homology to the transgene to be cloned, and the like) that will hybridize selectively with the transgene DNA. Another suitable method for obtaining a transgene is the polymerase chain reaction (PCR). However, successful use of this method requires that enough information about the nucleotide sequence of the transgene be available so as to design suitable oligonucleotide primers useful for amplification of the appropriate nucleotide sequence.

Where the method of choice requires the use of oligonucleotide primers or probes (e.g. PCR, cDNA or genomic library screening), the oligonucleotide sequences selected as probes or primers should be of adequate length and sufficiently unambiguous so as to minimize the amount of non-specific binding that will occur during library screening or PCR. The actual sequence of the probes or primers is usually based on conserved or highly homologous sequences or regions from the same or a similar gene from another organism. Optionally, the probes or primers can be degenerate.

In cases where only the amino acid sequence of the transgene is known, a probable and functional nucleic acid sequence may be inferred for the transgene using known and preferred codons for each amino acid residue. This sequence can then be chemically synthesized.

This invention encompasses the use of transgene mutant sequences. A mutant transgene is a transgene containing one or more nucleotide substitutions, deletions, and/or insertions as compared to the wild type gene sequence. The nucleotide substitution, deletion, and/or insertion can give rise to a gene product (i.e., protein) that is different in its amino acid sequence from the wild type amino acid sequence. Preparation of such mutants is well known in the art, and is described for example in Wells et al. (Gene, 34:315 (1985)), and in Sambrook et al, supra.

Selection of Regulatory Elements.

Transgenes are typically operably linked to promoters, where a promoter is selected to regulate expression of each transgene in a particular manner.

Where more than one transgene is to be used, each transgene may be regulated by the same or by a different promoter. The selected promoters may be homologous (i.e., from the same species as the mammalian cell or mammal to be transformed with the transgene) or heterologous (i.e., from a source other than the species of the mammalian cell or mammal to be transformed with the transgene). As such, the source of each promoter may be from any unicellular, prokaryotic or eukaryotic organism, or any vertebrate or invertebrate organism.

Selection of Other Vector Components

In addition to the transgene and the promoter, the vectors useful for preparing the transgenes of this invention typically contain one or more other elements useful for (1) optimal expression of transgene in mammalian cells into which the transgene is inserted, and (2) amplification of the vector in bacterial or mammalian host cells. Amplification of the transgene cassette involves use of an origin of replication in the construct suitable to the prokaryotic or mammalian cell host and expression in the cell of rep proteins. Each of these elements will be positioned appropriately in the vector with respect to each other element so as to maximize their respective activities. Such positioning is well known to the ordinary skilled artisan. The following elements may be optionally included in the vector as appropriate.

i. Signal Sequence Element

For those embodiments of the invention where the polypeptide encoded by the transgene is to be secreted, a small polypeptide termed signal sequence is frequently present to direct the polypeptide encoded by the transgene out of the cell where it is synthesized. Typically, the signal sequence is positioned in the coding region of the transgene towards or at the 5' end of the coding region. Many signal sequences have been identified, and any of them that are functional and thus compatible with the transgenic tissue may be used in conjunction with the transgene. Therefore, the nucleotide sequence encoding the signal sequence may be homologous or heterologous to the transgene, and may be homologous or heterologous to the ultimately rAAV-transduced mammalian cell or transgenic mammal receiving the rAAV virion. Additionally, the nucleotide sequence encoding the signal sequence may be chemically synthesized using methods set forth above. However, for purposes herein, preferred signal sequences are those that occur naturally with the transgene (i.e., are homologous to the transgene).

ii. Membrane Anchoring Domain Element

In some cases, it may be desirable to have a transgene expressed on the surface of a particular intracellular membrane or on the plasma membrane of a rAAV-transduced cell. Naturally occurring membrane proteins contain, as part of the polypeptide, a stretch of amino acids that serve to anchor the protein to the membrane. However, for proteins that are not naturally found on the membrane, such a stretch of amino acids may be added to confer this feature. Frequently, the anchor domain will be an internal portion of the polypeptide sequence and thus the nucleotide sequence encoding it will be engineered into an internal region of the transgene nucleotide sequence. However, in other cases, the nucleotide sequence encoding the anchor domain may be attached to the 5' or 3' end of the transgene nucleotide sequence. Here, the nucleotide sequence encoding the anchor domain may first be placed into the vector in the appropriate position as a separate component from the nucleotide sequence encoding the transgene. As for the signal sequence, the anchor domain may be from any source and thus may be homologous or heterologous with respect to both the transgene and the transgenic mammalian cell type or mammal intended to be transformed by the rAAV virion. Alternatively, the anchor domain may be chemically synthesized using methods set forth above.

iii. Origin of Replication ("Ori") Element

This component is typically a part of prokaryotic expression vectors purchased commercially, and aids in the amplification of the vector in a host cell. If the vector of choice does not contain an origin of replication site, one may be chemically synthesized based on a known sequence, and ligated into the vector.

iv. Transcription Termination Element

This element, also known as the polyadenylation or polyA sequence, is typically located 3' to the transgene nucleotide sequence in the vector, and serves to terminate transcription of the transgene. While the nucleotide sequence encoding this element is easily cloned from a library or even purchased commercially as part of a vector, it can also be readily synthesized using methods for nucleotide sequence synthesis such as those described above.

v. Intron Element

In many cases, transcription of the transgene is increased by the presence of one intron or more than one intron (linked by exons) on the cloning vector. The intron(s) may be naturally occurring within the transgene nucleotide sequence, especially where the transgene is a full length or a fragment of a genomic DNA sequence. Where the intron(s) is not naturally occurring within the nucleotide sequence (as for most cDNAs), the intron(s) may be obtained from another source. The intron(s) may be homologous or heterologous to the transgene and/or to the transgenic mammal. The position of the intron with respect to the promoter and the transgene is important, as the intron must be transcribed to be effective. As such, where the transgene is a cDNA sequence, the preferred position for the intron(s) is 3' to the transcription start site, and 5' to the polyA transcription termination sequence. Preferably for cDNA transgenes, the intron will be located on one side or the other (i.e., 5' or 3') of the transgene nucleotide sequence such that it does not interrupt the transgene nucleotide sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector. A preferred set of introns and exons is the human growth hormone (hGH) DNA sequence.

vi. Selectable Marker(s) Element

Selectable marker genes encode polypeptides necessary for the survival and growth of transfected cells grown in a selective culture medium. Typical selection marker genes encode proteins that (a) confer resistance to antibiotics or other toxins, e.g., ampicillin, tetracycline, or kanamycin for prokaryotic host cells, and neomycin, hygromycin, or methotrexate for mammalian cells; (b) complement auxotrophic deficiencies of the cell; or (c) supply critical nutrients not available from complex media, e.g., the gene encoding D-alanine racemase for cultures of *Bacillus* spp., e.g., *Bacillus stearothermophilus*.

All of the elements set forth above, as well as others useful in this invention, are well known to the skilled artisan and are described, for example, in Sambrook et al. (Molecular Cloning: A Laboratory Manual, Cold Spring Harbor Laboratory Press, Cold Spring Harbor, N.Y. (1989)) and Berger et al., eds. (Guide to Molecular Cloning Techniques, Academic Press, Inc., San Diego, Calif. (1987)).

Construction of Cloning Vectors

The cloning vectors most useful for amplification of pHelper, pTrans, and/or pCis plasmid cassettes useful in this invention are those that are compatible with prokaryotic cell hosts. However, eukaryotic cell hosts, including mammalian or insect cell hosts, and vectors compatible with these cells, are within the scope of the invention.

In certain cases, some of the various elements to be contained on the cloning vector may be already present in commercially available cloning or amplification vectors such as pUC18, pUC19, pBR322, the pGEM vectors (Promega Corp, Madison, Wis.), the pBluescript® vectors such as pBIISK+/− (Stratagene Corp., La Jolla, Calif.), and the like, all of which are suitable for prokaryotic cell hosts. In this case it is necessary to only insert the transgene(s) into the vector.

However, where one or more of the elements to be used are not already present on the cloning or amplification vector, they may be individually obtained and ligated into the vector. Methods used for obtaining each of the elements and ligating them are well known to the skilled artisan and are comparable to the methods set forth above for obtaining a transgene (i.e., synthesis of the DNA, library screening, and the like).

Vectors used for cloning or amplification of the transgene (s) nucleotide sequences and/or for transfection of the mammalian host cells are constructed using methods well known in the art. Such methods include, for example, the standard techniques of restriction endonuclease digestion, ligation, agarose and acrylamide gel purification of DNA and/or RNA, column chromatography purification of DNA and/or RNA, phenol/chloroform extraction of DNA, DNA sequencing, polymerase chain reaction amplification, and the like, as set forth in Sambrook et al., supra.

The final vector used to practice this invention is typically constructed from a starting cloning or amplification vector such as a commercially available vector. This vector may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector is to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

After the vector has been constructed, it may be transfected into a prokaryotic host cell for amplification. Cells typically used for amplification are *E. coli* DH5-alpha (Gibco/BRL, Grand Island, N.Y.) and other *E. coli* strains with characteristics similar to DH5-alpha.

Where mammalian host cells are used, cell lines such as human embryonic kidney cells (e.g., HEK 293) or Chinese hamster ovary (CHO cells; Urlab et al., Proc. Natl. Acad. Sci USA, 77:4216 (1980)) and human embryonic kidney cell line 293 (Graham et al., J. Gen. Virol., 36:59 (1977)), as well as other lines, are suitable.

Transfection of the vector into the selected host cell line for amplification is accomplished using such methods as calcium phosphate, electroporation, microinjection, lipofection or DEAE-dextran. The method selected will in part be a function of the type of host cell to be transfected. These methods and other suitable methods are well known to the skilled artisan, and are set forth in Sambrook et al., supra.

After culturing the cells long enough for the vector to be sufficiently amplified (usually overnight for *E. coli* cells), the vector (often termed plasmid at this stage) is isolated from the cells and purified. Typically, the cells are lysed and the plasmid is extracted from other cell contents. Methods suitable for plasmid purification include inter alia, the alkaline lysis mini-prep method (Sambrook et al., supra).

Preparation of Plasmid for Insertion

Typically, the plasmid containing the transgene is linearized, and portions of it removed using a selected restriction endonuclease prior to insertion into the mammalian host cell. In some cases, it may be preferable to isolate the transgene, promoter, and regulatory elements as a linear fragment from the other portions of the vector, thereby injecting only a linear nucleotide sequence containing the transgene, promoter, intron (if one is to be used), enhancer, polyA sequence, and optionally a signal sequence or membrane anchoring domain into the mammalian host cell. This may be accomplished by cutting the plasmid so as to remove the nucleic acid sequence region containing these elements, and purifying this region using agarose gel electrophoresis or other suitable purification methods.

Recombinant Production of Polypeptides of Interest.

Relevant amino acid sequences from a polypeptide of interest (e.g., an immunoglobulin) may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies). Relevant DNA sequences can be determined by direct nucleic acid sequencing.

Cloning of DNA is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the gene product of interest.

For example, one source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning. The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md. Isolated DNA can be operably linked to control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the polypeptide of interest, e.g., an antibody. An example of a signal sequence is:
ATGGACATGAGGGTGCCCGCTCAGCTCCTGGGGCT CCT GCTGCTGTGGC TGAGAGGTGCGCGCTGT//SEQ ID NO:1, which encodes the VK-1 signal peptide sequence MDMRVPAQLLGLLLLWLRGARC//SEQ ID NO:2), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

"Cell", "cell line", and "cell culture" are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Exemplary mammalian host cells include mammalian host cells that comprise a functional adenoviral E1A gene, either as a component of the parental cell line, such as in HEK 293, or by way of transformation of a different cell line of interest to include functionally expressed adenoviral E1A, and recombinant production of rAAV virions and other polypeptides of interest (including antibody) from such cells has become routine procedure. Other examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); A549 cells (ATCC® CCL-185™; adenocarcinomic human alveolar basal epithelial cells; see, Farson et al., Development and characterization of a cell line for large-scale, serum-free production of recombinant adeno-associated viral vectors, J Gene Med. 6(12):1369-81 (2004)); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68 (1982)); MRC 5 cells or FS4 cells; or mammalian myeloma cells.

Mammalian host cells are transformed or transfected with the above-described nucleic acids or vectors for production of rAAV virions and, optionally other polypeptides of interest (including antibodies or antibody fragments, enzymes, hormones, cytokines, chemokines, receptors, etc.), and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of polypeptides.

The mammalian host cells used to produce the recombinant AAV virions according to the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. No. 4,767,704; 4,657, 866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the recombinant polypeptide can be produced intracellularly, in the periplasmic space, or directly secreted into the medium. If the polypeptide, such as an antibody, is produced intracellularly, as a first step, the particulate debris, either host cells or lysed fragments, is removed, for example, by centrifugation or ultrafiltration.

Recombinant AAV virions and other polypeptides of interest, such as but not limited to, an antibody or antibody fragment, enzyme, ion channel, hormone, cytokine, chemokine, receptor, or toxin peptide) can be purified using, for example, hydroxylapatite chromatography, Sepharose® chromatography, cation or anion exchange chromatography, or preferably affinity chromatography, using the antigen of interest or protein A or protein G as an affinity ligand. Protein A can be used to purify proteins that include polypeptides that are based on human γ1, γ2, or γ4 heavy chains (Lindmark et al., J. Immunol. Meth. 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a $C_H3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered. Other purification methods useful in practicing the invention are known in the art or described herein.

Examples of embodiments of the invention include the following:

Embodiment 1

An in vitro method of producing a recombinant AAV virion in a mammalian host cell, comprising incubating the cell in a transfection medium comprising:
(i) an accessory construct comprising a plasmid (pHelper) comprising adenoviral E2, E4Orf6, and VAI RNA genes operably linked to an origin of replication element and one or more other regulatory sequences;
(ii) an AAV helper construct comprising a plasmid (pTrans) comprising AAV rep and AAV cap coding regions operably linked to one or more regulatory sequences; and
(iii) a AAV vector comprising a plasmid (pCis), comprising AAV inverted terminal repeats flanking a heterologous gene of interest operably linked to one or more regulatory sequences,
wherein the ratio of pHelper:pTrans:pCis is 1:1 to 5:0.009 to 0.36 (weight:weight:weight).

Embodiment 2

The method of Embodiment 1, wherein the mammalian host cell is a HEK 293 cell.

Embodiment 3

The method of Embodiment 2, wherein the HEK 293 cell is suspended in the transfection medium.

Embodiment 4

The method of Embodiment 3, wherein the HEK 293 cell is suspended at a cell density of 2.1-3.0×10$^6$ cells/mL.

Embodiment 5

The method of Embodiment 4, wherein the HEK 293 cell is suspended at a cell density of 2.2-2.7×10$^6$ cells/mL.

Embodiment 6

The method of Embodiment 5, wherein the HEK 293 cell is suspended at a cell density of about 2.5×10$^6$ cells/mL.

Embodiment 7

The method of Embodiments 1-2, wherein the cell adheres to a solid substrate.

Embodiment 8

The method of Embodiment 1, wherein transfection medium comprises tryptone N1 (TN1) at a concentration of 1.4-1.6% (w/v).

Embodiment 9

The method of Embodiment 8, wherein the tryptone N1 (TN1) is at a concentration of 1.475-1.525% (w/v).

Embodiment 10

The method of Embodiments 1-9, wherein the transfection medium comprises 0-20 mM sodium butyrate.

Embodiment 11

The method of Embodiments 1-10, wherein the ratio of pHelper:pTrans:pCis is 1:1 to 5:0.30 to 0.36 (weight:weight:weight).

Embodiment 12

The method of Embodiment 11, wherein the ratio of pHelper:pTrans:pCis is 1:5:0.31 (weight:weight:weight).

Embodiment 13

A recombinant AAV virion made by the method of any of Embodiments 1-12.

The invention will be more fully understood by reference to the following examples. These examples are not to be construed in any way as limiting the scope of this invention.

EXAMPLES

Example 1

Materials and Methods

Cell Culture:

Suspension HEK293T cells were cultured in a 125-ml Erlenmeyer flask (Corning) agitated at 110 rpm. HEK293T cells were grown in 20 ml of FreeStyle™ 293 Expression Medium (Life Technologies; Durocher et al., Scalable serum-free production of recombinant adeno-associated virus type 2 by transfection of 293 suspension cells, J Virol Methods 144:32-40 (2007)) supplemented with 2% FBS and 50 mg/L G418, and 293-6E cells were cultured in Free-Style™ F17 Expression Medium (Life Technologies) supplemented with 6 mM glutamine, 0.1% F68 and 25 mg/L G418. For rAAV vector production in large scale, cells were cultured in 1 L of the same medium in a 3 L Erlenmeyer flask agitating at 65 rpm. Adherent HEK293T cells were cultured in DMEM medium supplemented with 10% FBS (Luk et al., Efficient Serotype-Dependent Release of Functional Vector into the Culture Medium During Adeno-Associated Virus Manufacturing, Efficient Serotype-Dependent Release of Functional Vector into the Culture Medium During Adeno-Associated Virus Manufacturing, Hum Gene Ther. 21: 1251-1257 (2010)) and penicillin (100 units/mL), streptomycin (100 μg/mL), and glutamine (0.292 mg/mL).

Plasmid Construction:

pTrans2 was generated by subcloning of the DNA fragment encoding the rep and cap ORF from the AAV2 genome into pBluescript II (Agilent Technologies) and modifications were introduced upstream of the rep ORF to enhance AAV cap gene expression. The pTrans2/8 and pAGL2/8 were constructed by replacing the cap ORF in pTrans2 and pAAV-RC with the AAV8 cap ORF, respectively.

Recombinant AAV Vector Production in Suspension Cells:

Cells were transfected using PEIMAX (Polyscience) with three plasmids (pHelper, pTrans and pCis-EGFP). Brief maps of the plasmids are shown in FIG. 1. Plasmids were mixed in OptiMEM (Life Technologies, 1/20 volume of the cells to be transfected) and incubated for 5 min. PEIMAX was then added to DNA diluted in OptiMEM, and, after incubation for an additional 10 min, the DNA-PEIMAX complex was added to the cells. Twenty four hours post transfection, sodium butyrate and protein hydrolysate (in this case Tryptone N1 [TN1], a controlled enzymatic hydrolysis of casein; Organotechnie® S.A.S.; see, Pham et al., Biotechnol Bioeng 90: 332-344 (2005])) were added to the culture, and rAAV vectors were harvested 72 h post transfection. For large scale production of rAAV2/8 vectors, rAAV2/8 vectors in both the cells and medium were harvested.

Recombinant AAV Vector Production in Adherent Cells:

For large scale rAAV vector production, cells in a Cell-STACK® cell culture chamber (CS, 10 layers, 6360 cm$^2$, Corning) were transfected with 4 mg (plasmid ratio 2:1:1), or 3 mg (plasmid ratio 1:5:0.31) of total DNA using a CaPO$_4$ method in 2 L of DMEM with 2% fetal bovine serum (FBS), penicillin (100 units/mL), streptomycin (100 μg/mL), and glutamine (0.292 mg/mL). After 24 hours, the transfection medium was replaced with 1 L of fresh DMEM supplemented with TN1 and sodium butyrate, and rAAV2/8 vectors in cells and medium were harvested at 72 hours post transfection.

Purification of rAAV2/1, 2, 2/5, and 2/8 Vectors:

For large scale production, rAAV2/8 vectors in the medium were precipitated as previously described with polyethylene glycol (PEG) (Sigma) and NaCl, and cells were lysed by freezing/thawing 3 times. The cell lysate and medium were then combined (the starting material), and adjusted to pH 5.5 to precipitate proteins. After centrifugation at 12000 g, the pH was adjusted to 8.0 and the starting material was filtered through a 0.2 μm filter. The rAAV vectors were then loaded onto an AVB Sepharose column and eluted with Glycine-HCl (pH 3.0). The eluted rAAV vector was immediately neutralized with 1M Tris-HCl (pH 8.0) and dialyzed against phosphate buffered saline (PBS)-MK buffer (PBS with 1 mM MgCl$_2$ and 2.5 mM KCl). Purified rAAV vectors were then concentrated to a desired concentration in dialysis cassettes with Slide-A-Lyzer Concentrating Solution (Thermo Fisher).

DNA Dot Blot Analysis:

Cell lysates were loaded onto Nylon membrane and hybridized overnight with a $^{32}$P-labeled EF1α promoter specific probe. After washing, the intensity of radioactivity was measured using a Storm A60 Scanner.

rAAV Titration Using CyQuant:

Purified rAAV2/8 vectors from large scale production were routinely titered using the QuickTiter AAV Quantitation Kit (Cell Biolabs, INC).

rAAV Titration Using bDNA Assay:

For quantification of rAAV2/1, 2, 2/5, or 2/8 produced in 20 ml cultures, rAAVs in cell lysates were first purified with AVB Sepharose, and then the QuantiGene2.0 assay (Branched DNA Technology) was used to determine the GCs of rAAV using a rAAV prep with known viral GC as standard. The EF1α and the CMV promoter specific probe sets for pCis-EGFP, pAAV-LacZ, and pAAV-empty were used. Serially diluted viral preps were incubated in lysis buffer with a specific probe set in bDNA capture plates at 55° C. for overnight hybridization and then chemiluminescent signals were read in a Perkin Elmer EnVision as previously reported.

Statistical Method:

All experimental designs and statistical analyses were performed using JMP version 7.0.2 and version 9.0.0 under the Windows Vista System. For the purpose of characterizing the impact of cell density, total DNA amount, ratio of Plasmid 1 (pHelper) to Plasmid2 (pTrans) and ratio of Plasmid 1 to Plasmid 3 (pCis) on the production of rAAV2/8 vector in suspension HEK293T cells and maximizing such production with regard to these factors with TN1 and sodium butyrate fixed. Two response surface design experiments (40 runs fixing Ratio of PEIMAX to total DNA amount) were performed and statistically analyzed. For the purpose of improving production of rAAV2/8 vector in HEK293T suspension cells with regard to TN1 and sodium butyrate given the factor levels determined from previous two response surface experiments, a response surface experiment (28 runs) was performed and statistically analyzed.

SDS-PAGE and Immunoblot:

Proteins in cell lysates were separated on a 4-20% reducing Tris-Glycine gel (Life Technologies). Following transfer, membranes were probed with anti-VP1, 2, 3 mAb (Fitzgerald Industries Inc.) and incubated with Alexa Fluor 680 goat anti-mouse IgG (Life Technologies). Protein bands were visualized on an Odyssey Scanner (LiCor).

Example 2

Improvement of rAAV Vector Production

We improved rAAV2/8 vector production by employing a design-of-experiment (DOE) multivariable analysis approach. The DOE approach can be advantageous over the one-factor-at-a-time (OFAT) method because it requires fewer resources (experiments, time, material, etc.) for the amount of information obtained. Also, the estimates of the effects of each factor are more precise and the interaction between factors can be estimated systematically.

Figure 2B:
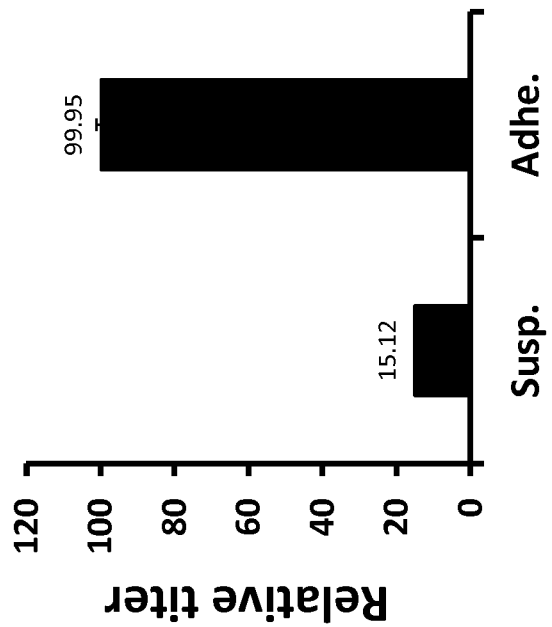
FIG. 2A-B illustrates that optimized conditions for rAAV2/5 vector production in suspension cells generated by a one-factor-at-a-time (OFAT) method did not result in efficient rAAV2/8 vector production.

1. Improved parameters from an OFAT method for rAAV2/5 vector production did not yield efficient rAAV2/8 vector production. We improved rAAV2/5 production in suspension HEK293T cells using an OFAT method. This study of rAAV2/5 vector production revealed the optimal parameter values of cell density at $0.5 \times 10^5$ cells/ml, plasmid concentration at 1.5 μg/ml, and harvest time at 72 h, similar to the published methods for rAAV2 vector productions (Durocher Y, Pham P L, St-Laurent G, Jacob D, Cass B, Chahal P, Lau C J, Nalbantoglu J, Kamen A. Scalable serum-free production of recombinant adeno-associated virus type 2 by transfection of HEK293 suspension cells. J. Virol. Methods. 144:32-40 (2007)). We also demonstrated that addition of Tryptone N1 (TN1) and sodium butyrate 24 hours after transfection increased rAAV2/5 vector production based on Immunoblot analysis for AAV5 capsid proteins (VP1, VP2 and VP3). By using these optimal conditions in suspension cells, we achieved rAAV2/5 vector GC production levels equivalent to those from adherent HEK293T cells (Zhao H, Wolf T, van der Valk M, Plewa C A, Sheng J, Lee K J. Cost effective and facile method of rAAV production in suspension-adapted HEK293 cells. Mol. Ther. 19, Supplement 1:S257 (2011)). However, when these optimal conditions were applied to rAAV2/8 vector production, production yields were much lower than those from adherent HEK 293T cells based on both Immunoblot analysis of VPs in the cell lysate (FIG. 2A) and quantification of genome copies (GC) after purification with AVB Sepharose (FIG. 2B). Initial attempts at improving rAAV2/8 vector production using the OFAT method was not successful (data not shown). Thus, a design-of-experiment (DOE) multivariable analysis approach was employed for improvement of rAAV2/8 vector production.

2. Production yield of rAAV2/8 vector by a DOE-improved method in suspension cells is comparable to adherent cells and uses a lower amount of DNA. We studied a variety of parameters using a DOE approach, including cell density, total amount of DNA, and plasmid ratios (pHelper: pTrans2/8 and pHelper:pCis-eGFP). The ranges of these parameters used for experimental design are shown in Table 1 below.

TABLE 1

Design of experiment (DOE). All transfections were carried out in 125-ml Erlenmeyer flasks. Transfection volume was 20 ml. Forty runs include duplicates.

| Parameters | Variation ranges |
| --- | --- |
| Cell density ($\times 10^6$/ml) | 0.25-4.0 |
| Total amount of DNA (mg/L) | 0.5-3.5 |
| pHelper:pTrans2/8 | 1:5-1:0.2 |
| pHelper:pCis-EGFP | 1:5-1:0.16 |
| PEIMAX:DNA | 3:1 (fixed) |
| Trypton N1 (TN1) | 0.5% w/v (fixed) |
| Sodium Butyrate | 5 mM (fixed) |

The ratio of PEIMAX to the amount of DNA (3:1) is well established and therefore was not studied here. TN1 and sodium butyrate were included as these additives promoted capsid protein expression in our previous OFAT optimization for rAAV2/5 vector production and were kept constant in the design to reduce the number of variables and runs (Zhao H, Wolf T, van der Valk M, Plewa C A, Sheng J, Lee K J. Cost effective and facile method of rAAV production in suspension-adapted HEK293 cells. Mol. Ther. 19, Supplement 1:S257 (2011)). The study employing a DOE approach was carried out in 20 ml of suspension HEK293T cells using enhanced green fluorescence protein (eGFP) as the gene of interest (GOI). TN1 and sodium butyrate were added 24 h post transfection. The GCs of rAAV2/8 vectors in the cell lysate were determined by Dot blot analysis, and the data were analyzed with JMP software. DOE revealed a novel set of parameter values as compared to both published and our own OFAT-optimized methods for rAAV2/5 production (Table 2; below).

TABLE 2

Comparison of optimal values of DOE with published rAAV2 and experimental rAAV2/5 vector production conditions.

| Factors | Published susp. conditions* rAAV2 | Experimental Suspension Conditions rAAV2/5 (OFAT)[&] | Experimental Suspension Conditions rAAV2/8 (DOE) | Experimental cell stack conditions |
| --- | --- | --- | --- | --- |
| Cell density ($\times 10^6$/mL) | 0.5-1 | 0.5 | 2.45 | N/A |
| DNA amount | 1-1.25 mg/L | 1.5 mg/L | 1.5 mg/L | 4 mg/6300 cm$^2$ |
| Plasmid ratio*[#] | 1:1:1 or 2:1:1 | 2:1:1 | 1:5:0.31 | 2:1:1 |
| PEI:DNA | 2:1, 3:1 | 3:1 | 3:1 | N/A (CaPO$_4$) |

N/A = not applicable;
*Hildinger, M., et al. Biotechnol. Lett. 2007; 29: 1713-172, Durocher Y., et al. J. Virol. Methods 2007; 144: 32-40;
[#]Plasmid ratio: pHelper:pTrans:pCis; & Zhao, H. et al., Mol. Ther. 19, Supplement 1:S257 (2011).

Figure 3B:
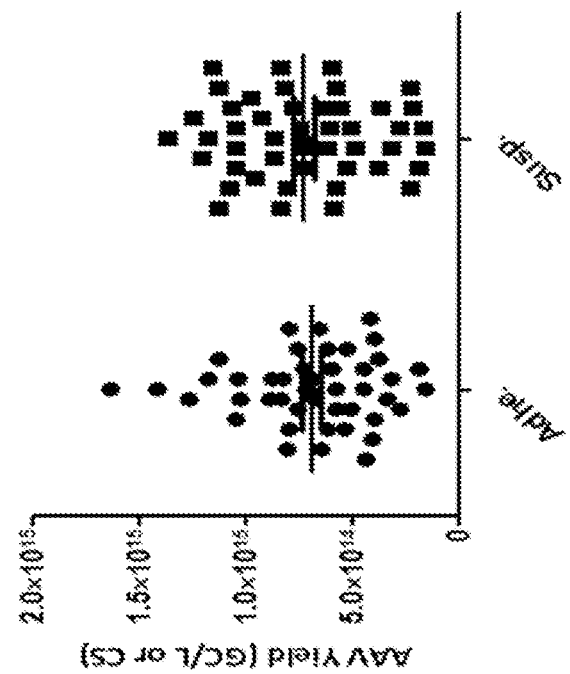
Figure 3A:
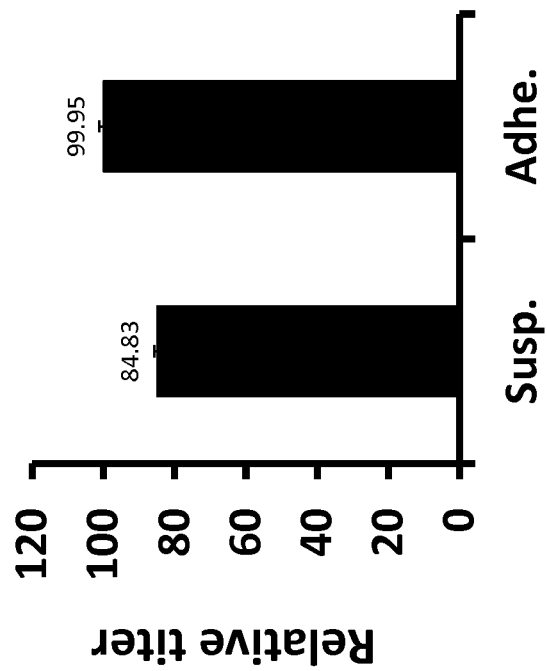

Notably, the innovative plasmid ratio 1:5:0.31 (pHelper: pTrans:pCis, weight:weight) is divergent from published ratios reported for adherent cells (1:1:1 or 2:1:1) or for suspension cells (1:1:1 or 3:1:1); and the cell density (2.45× $10^6$ cells/ml) is higher than in published methods (0.5-1×$10^6$ cells/ml). These parameter values were then used to produce rAAV2/8-eGFP in 1 L scale, and the yield (GC/L) was determined using the CyQuant titration method. As shown in FIG. 3A, the amount of rAAV2/8-eGFP produced in 1 L suspension is comparable to that from a 10-layer Cell-STACK® cell culture chamber (6360 cm$^2$). This method was then applied to large scale productions for many GOIs. As shown in FIG. 3B, average production yields were equivalent to those from adherent HEK293T cells. In addition to the higher yield than that from the OFAT optimized protocol (FIG. 2B), the combination of lower total DNA amount and the novel plasmid ratio allows us to reduce the of total amount of DNA to 62.5% of previous, 92.6% of pCis-GOI and 88.1% of pHelper as compared to the amounts used for adherent cells (FIG. 3C). Reduction of the amount of pHelper and pCis-GOI used in rAAV2/8 vector production will significantly ease the process.

Figure 5:
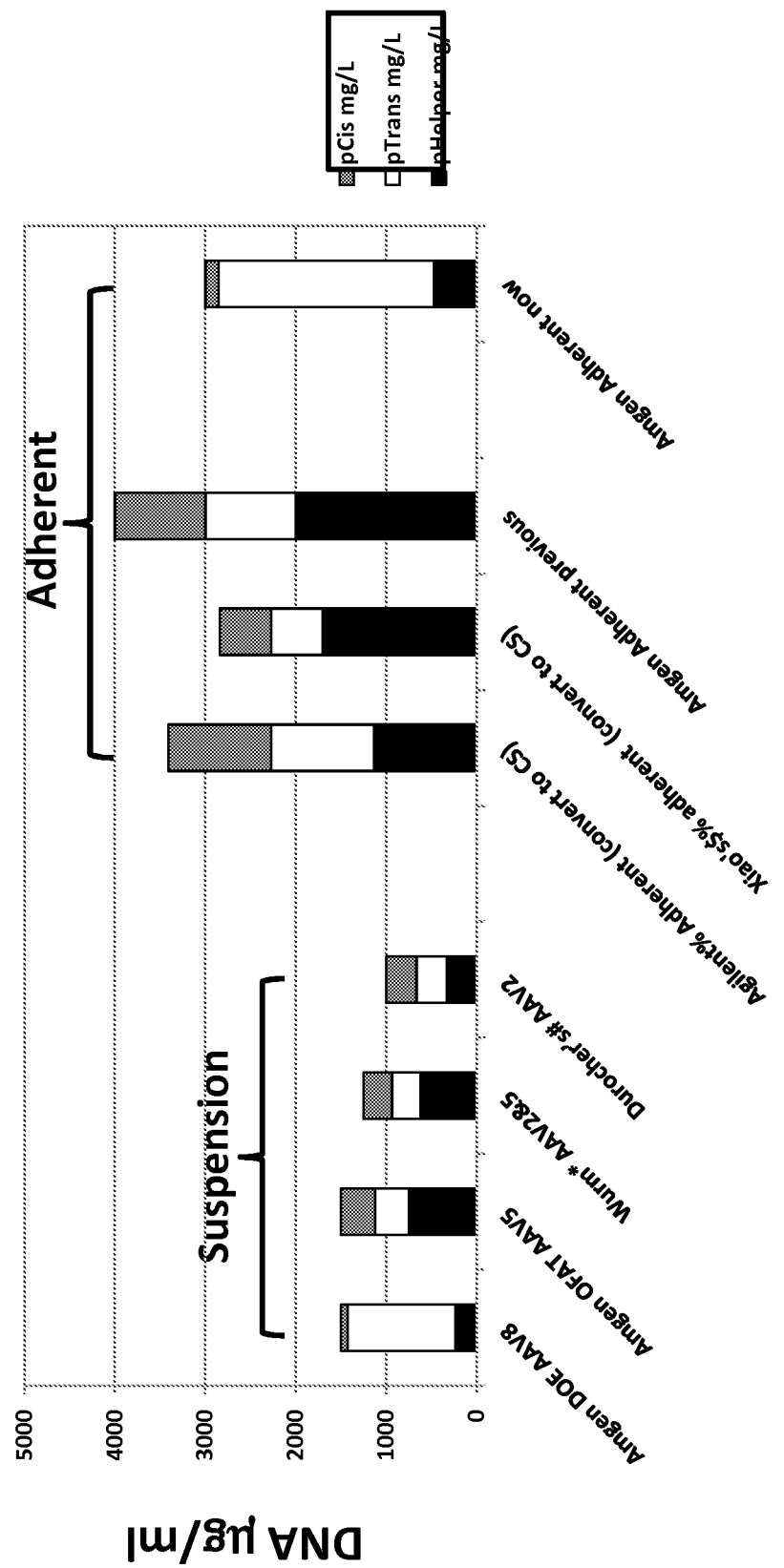
FIG. 5 shows a comparison of the amount of plasmid DNAs used for rAAV vector production in various protocols. "*" Durocher Y., et al. J. Virol Methods 144:32-40 (2007); "#" Hildinger, M., et al. Biotechnol Lett. 29:1713-1721 (2007); "$" Xiao et al. J Virol. 72:2224-32 (1998); "&" Cell density is 2×10$^6$/ml at transfection, diluted to 1×10$^6$ at 4 hours after transfection; "%" Agilent Technologies Inc' (Cat 240071) and Xiao et al.'s (Xiao et al. J Virol. 72:2224-32 (1998)) protocols were converted to cell stack ["CS"] scale based on surface area of the cell culture chamber (CellSTACK®-10: 6360 cm$^2$, 100 mm dish: 55 cm$^2$; Corning Life Sciences, Lowell, Mass.).

3. The novel plasmid ratio revealed by the DOE analysis in suspension cells can also be applied to adherent cells. To test if the novel plasmid ratio can be used for rAAV production in adherent HEK293T cells, we transfected adherent HEK293T cells in a 10-layer CellSTACK® cell culture chamber using a calcium phosphate protocol with either the existing plasmid ratio (2:1:1, pHelper:pTrans: pCis, total 4 mg DNA in 2 L of medium [2 mg/L]) or the newly established plasmid ratio (1:5:0.31, total 3 mg DNA in 2 L of medium [1.5 mg/L]). The medium was replaced with 1 L fresh medium 24 h post transfection. Production yields with the new plasmid ratio were comparable to the standard protocol as judged by total GC (FIG. 4A). Again, the major advantage of using the new plasmid ratio is significant reduction of the amount of total DNA (down 25%), pHelper (down 76%) and pCis-GOI (down 85%), while the amount of pTrans was increased considerably (up 138%, FIG. 4B). The amount of plasmids used in rAAV vector production using either suspension or adherent cells from previously published and Amgen's in house data are summarized in FIG. 5.

Figure 2A:
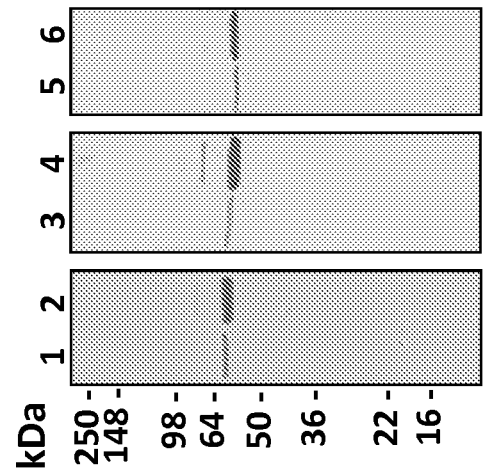
Figures 6A, 6B:
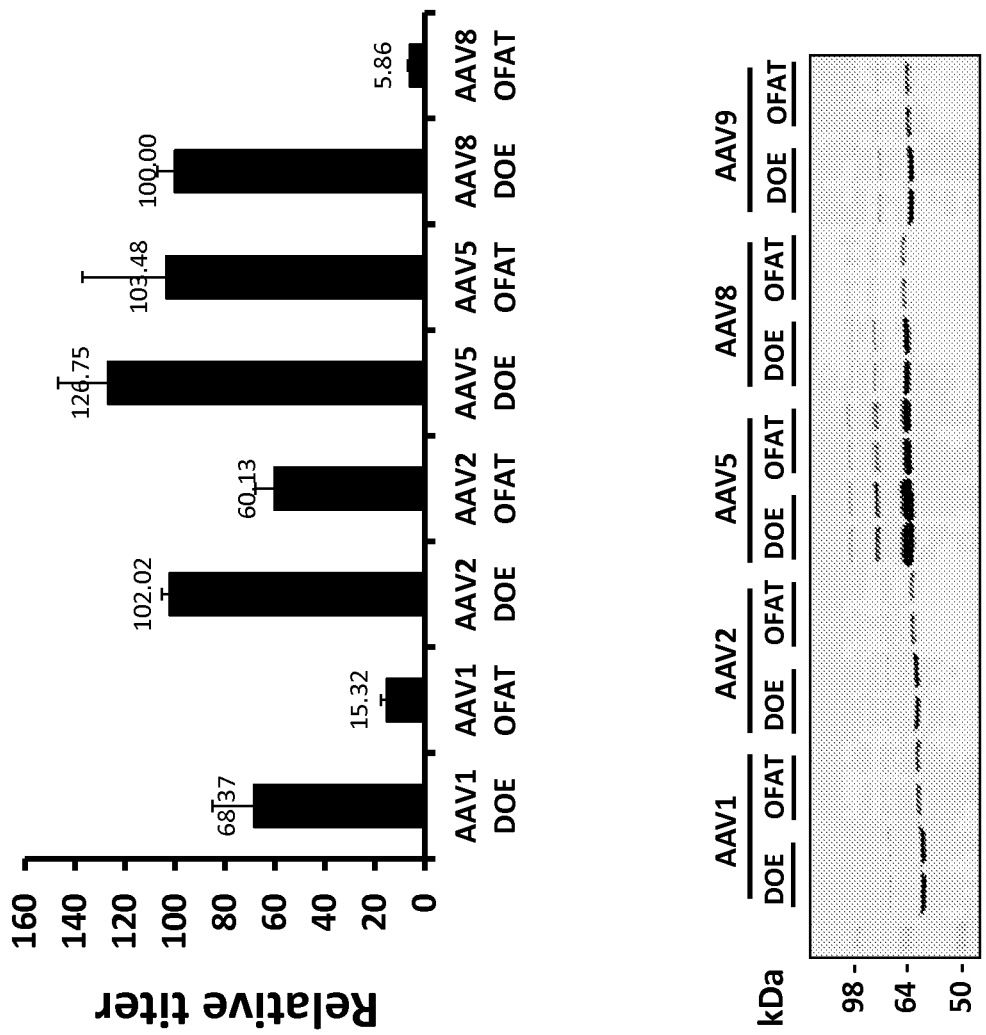
FIG. 6A-B illustrates that the optimized protocol for rAAV2/8 vector production identified by DOE can also be applied to production of serotypes rAAV2/1, 2, 2/5 and 2/9 in suspension cells. Twenty milliliters of suspension HEK293T cells were transfected using either the OFAT— (optimized for rAAV2/5 vector production) or DOE—(optimized for rAAV2/8 vector production) optimized protocols as described in Example 1 herein (Materials and Methods) and Table 2. At 72 hours post-transfection, the relative titers (FIG. 6A) and capsid proteins (FIG. 6B) in cell lysates were analyzed by bDNA assay and Immunoblot, respectively. The bars represent the average of duplicates.

4. The improved production protocol determined for serotype 8 can also be applied to rAAV 2/1, 2, 2/5 and 2/9 serotypes produced in suspension cells. Next we attempted to determine if the DOE-improved method could be used for production of other rAAV serotypes besides rAAV2/8, e. g. rAAV2/1, 2, 2/5, and 2/9. To this end, rAAV2/1, 2, 2/5, and 2/9 were generated in 20 ml of suspension HEK293T cells using either the DOE-improved protocol or our previously described OFAT-optimized protocol for rAAV2/5 vector production (Table 2). The total GCs and capsid proteins in the lysates were analyzed by bDNA assay and Immunoblot, respectively. As shown in FIG. 6A, significantly more GCs were produced using the DOE-improved method for rAAV2/1 (4.5 times), 2/2 (1.7 times) and 2/8 (17 times). Similar trends were observed when vector production was quantified by Immunoblot (FIG. 6B). Since rAAV2/9 vectors do not bind to AVB Sepharose (data not shown), we were unable to purify and analyze them by bDNA assay. Therefore, we relied solely on the Immunoblot assay for quantitation of production. Again, more rAAV2/9 capsid proteins were detected in samples produced using the DOE-improved protocol than that in those produced using the OFAT-optimized protocol. There was variability in the total production yields of rAAV2/8 vectors between experiments although the DOE-improved method resulted in consistently higher production yields (FIG. 6A: 17 folds and FIG. 2A: 5-6 folds). The variability could be due to slight differences in production and/or purification scales or the titration methods used in these experiments. Overall production yield using the DOE-improved protocol is superior to that from the OFAT-optimized protocol, especially for rAAV2/1 and 2/8 production. It will be interesting to know if these findings can be extended to other serotypes such as AAV3, 4, 6, and 7.

Figure 7A:
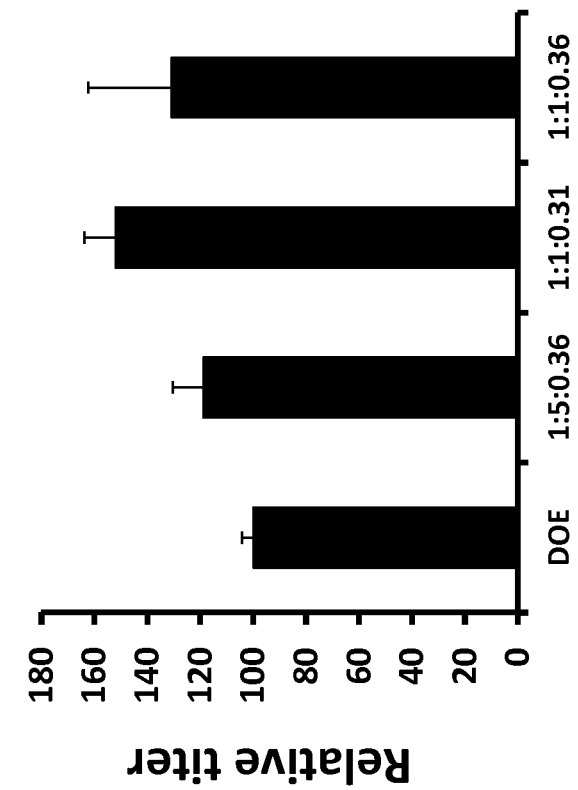
FIG. 7A-B demonstrates production of rAAV2/8 and rAAV2 vectors using plasmid ratios predicted to produce 90% or greater of the optimal yield. Predicted plasmid ratio ranges are from Table 3. rAAV vectors were produced in suspension cells, using the DOE-optimal plasmid ratio or alternative ratios predicted to produce 90% of optimal yield. rAAV2/8-eGFP (A) or rAAV2-eGFP (B) were produced in 20-ml cultures and purified with AVBSepharose (GE Healthcare Life Sciences) from cell lysates. GC/ml was determined by bDNA assay. The bars represent the average of duplicates.
Figure 7B:
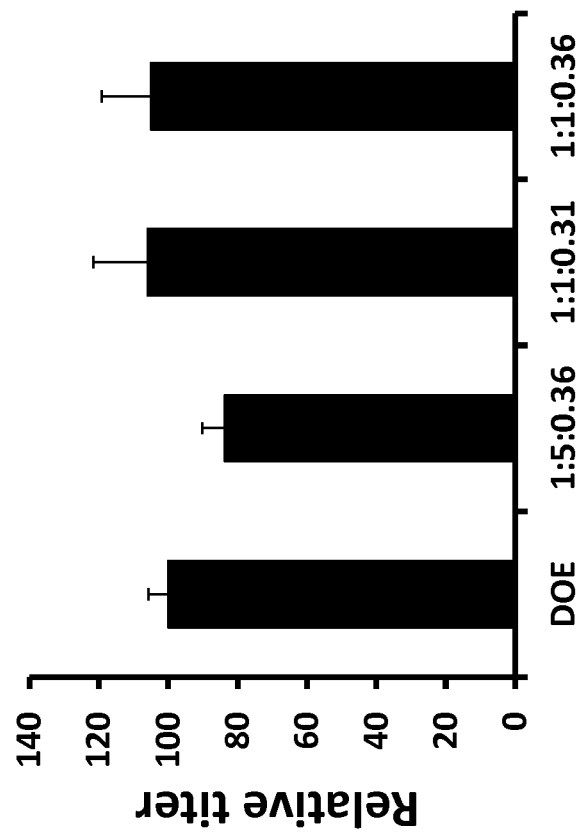

5. Using plasmid ratios predicted to be greater than 90% of the maximal production of rAAV vector yields similar amount of rAAV vector as compared to the DOE-improved ratio. Since the plasmid ratio identified using DOE optimization is unique compared to other published ratios, we tried to define the range of ratios that produce similar amounts of vector to using the optimal value. First, we calculated the range of plasmid ratios resulting in production yields within 90%, 80%, and 70% of the optimal ratio (see, Table 3A; below). Then we experimentally tested the production yields using the plasmid ratios predicted to produce 90% of the optimal yield, while keeping the total amount DNA (1.5 μg/ml) unchanged (see, Table 3B, below). As shown in FIG. 7, production yields of rAAV2/8-eGFP obtained from these ratios were similar to those from the optimal ratios. In the case of rAAV2-eGFP production, slightly more rAAV2 vector was produced with the ratio of 1:1:0.31, possibly because the original optimization was for rAAV2/8, not rAAV2. These results suggest that a broader range of plasmid ratios could result in similar enhanced production yields of rAAV.

TABLE 3A

Predicted range of parameters for 90%, 80%, and 70% of optimal rAAV8 production. Plasmid ratios are based on weight

| Parameters | 70% range | 80% range | 90% range | Optimal |
|---|---|---|---|---|
| DNA amount (μg/mL) | 1.5-2.1 | 1.5-2.3 | 1.5-2.3 | 1.5 |
| Cell density (×$10^6$/mL) | 1.2-3.8 | 1.15-3.6 | 1.4-3.7 | 2.45 |
| pHelper:pTrans | 0.2-2.5 | 0.2-1.5 | 0.2-1 | 0.2 |
| pHelper:pCis | 1.9-3.9 | 2.7-3.5 | 2.8-3.3 | 3.23 |

TABLE 3B

Plasmid ratios predicted to produce 90% of the optimal yield

| Parameters | Plasmid ratio of 90% range |
|---|---|
| pHelper:pTrans | 1:5:0.31 |
|  | 1:5:0.36 |
| pHelper:pCis | 1:1:0.31 |
|  | 1:1:0.36 |

Figure 8A:
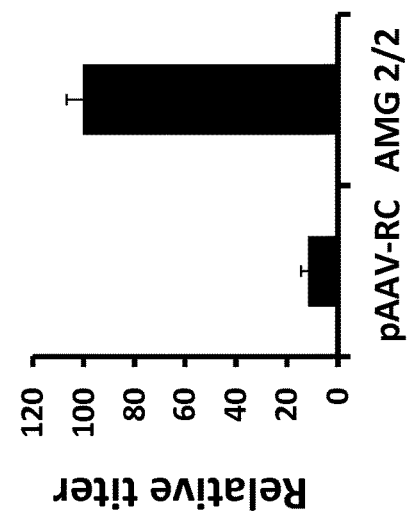
FIG. 8A-C shows a comparison of customized rAAV plasmids ("AMG") with commercially available and published plasmids in rAAV2/8 and rAAV2 production using the DOE optimized protocol. In all experiments, rAAV2 or rAAV2/8 vectors were produced in 20-ml cultures, which were then purified with AVB Sepharose from cell lysates and the GC/ml was determined by bDNA assay.
Figure 8B:
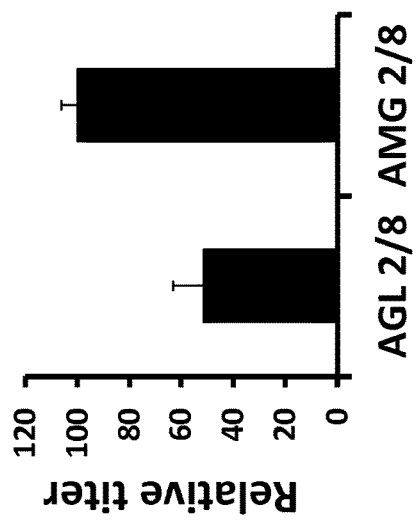
Figure 8C:
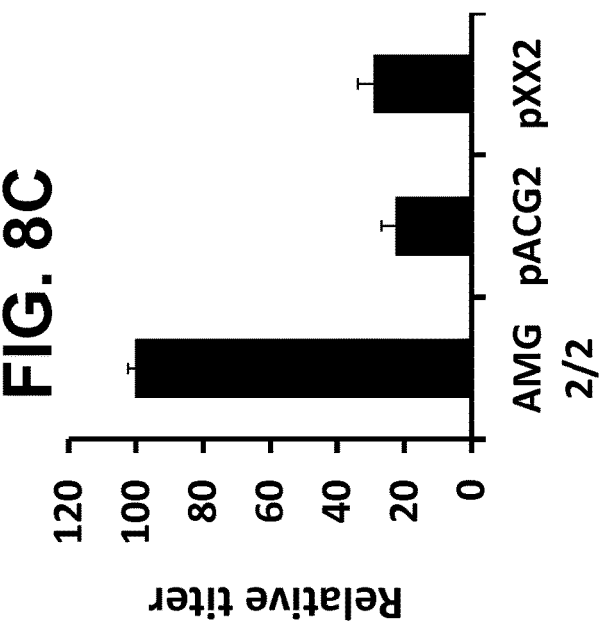

6. The DOE-improved protocol can be used with Agilent's plasmid system for rAAV2/8 vector production, but not rAAV2. As described in Materials and Methods, the pTrans plasmid used in our studies is extensively modified (and different from pACG2). To broaden the application of our newly established protocol to rAAV plasmids systems beyond our own, we tested rAAV vector production with our protocol using commercially available and published plasmids. First, the plasmids from Agilent's AAV Helper-Free System were tested. Since Agilent only has pAAV-RC for rAAV2, we replaced the cap gene of AAV2 in pAAV-RC with the cap gene of AAV8 (pAGL2/8). Both rAAV2- and rAAV8-LacZ vectors produced using Agilent's plasmids were compared with the yields of rAAV2- and rAAV8-eGFP vectors using our in-house plasmids. The use of pAGL2/8 and pAAV2-RC yielded about 50% and 89% less rAAV2/8 and rAAV2 vectors, respectively, as compared with Amgen's plasmids (FIGS. 8A and B). Thus, the DOE-improved conditions could be used in rAAV2/8 vector production with reduced yield, but yield was significantly compromised for the rAAV2 vector. Second, we tested two published pTrans vectors (pACG2 and pXX2) (Xiao X, Samulski R J. Production of high-titer recombinant adeno-associated virus vector in the absence of helper adenovirus. J. Virol. 72:2224-2232 (1998)). Our results showed that vector production using commercially available pACG2 and pXX2 only yielded 22.4% and 29.0% of rAAV2-EGFP vectors, respectively, as compared to our own recombinantly obtained plasmids (FIG. 8C).

7. Comparison of suspension HEK293T and HEK293-6E cells in the DOE-improved protocol. To investigate if other suspension HEK293 cell lines could be used in DOE-improved protocol for rAAV2 and 2/8 production, we replaced HEK293T suspension cells with HEK293-6E cells that stably express the Epstein-Barr virus nuclear antigen-1 (HEK293-EBNA1) because it was a previously reported host cell line used for rAAV2 vector production (Durocher Y, Pham P L, St-Laurent G, Jacob D, Cass B, Chahal P, Lau C J, Nalbantoglu J, Kamen A. Scalable serum-free production of recombinant adeno-associated virus type 2 by transfection of 293 suspension cells. J Virol Methods. 144:32-40 (2007)). The relative GCs in cell lysates from both DOE- and OFAT-optimized protocols were determined by bDNA assay. The results showed that HEK293-6E cells produced much less rAAV2 and rAAV2/8 as compared to HEK293T cells (FIG. 9A). This was further confirmed by Immnoblotting of capsid proteins as shown in FIG. 9B. The reason for this is not clear. We have previously observed that HEK293-6E cells have lower transfection efficiency than that of HEK293T cells (Zhao H, Wolf T, van der Valk M, Plewa C A, Sheng J, Lee K J. Cost effective and facile method of rAAV production in suspension-adapted HEK293 cells. Mol. Ther. 19, Supplement 1:S257 (2011)). This could be an important factor responsible for lower yield of rAAV vectors in HEK293-6E cells.

8. Comparison of the DOE-improved protocol to a published OFAT-optimized protocol. Next, we compared a published protocol (Durocher Y, Pham P L, St-Laurent G, Jacob D, Cass B, Chahal P, Lau C J, Nalbantoglu J, Kamen A. Scalable serum-free production of recombinant adeno-associated virus type 2 by transfection of HEK293 suspension cells. J Virol Methods. 144:32-40 (2007)) with our DOE-improved protocol in terms of the yield of rAAV2 and rAAV2/8 vector production in suspension cells. The detailed comparison between the DOE-improved protocol and Durocher's method was described in Table 4 (below).

TABLE 4

Comparison Durocher's OFAT optimized method (Durocher, Y et al., Scalable serum-free production of recombinant adeno-associated virus type 2 by transfection of 293 suspension cells. J Virol Methods. 144: 32-40 (2007)) with DOE optimized method. In this experiment, HEK 293T cells and medium were used in Durocher's method, and harvest at 72 h post-transfection.

| Parameters | Durocher's | Described herein |
|---|---|---|
| Cell Line | HEK 293F | HEK 293T |
| Medium | Freestyle™ 293 Expression Medium, 0.1% F68 | Freestyle™ 293 Expression Medium, 2% FBS |
| Cell density at transfection ($\times 10^6$/mL) | 0.5 | 2.5 |
| Total DNA (µg/mL) | 1 | 1.5 |
| Ratio (pHelper:pTrans:pCis) | 1:1:1 pHelper - Agilent pCis - Agilent pTrans - pACG2 | 1:5:0.31 As described herein |
| TN1 and sodium butyrate | No | Yes |
| Harvest post-transfection (hours) | 48 | 72 |

Figure 10A:
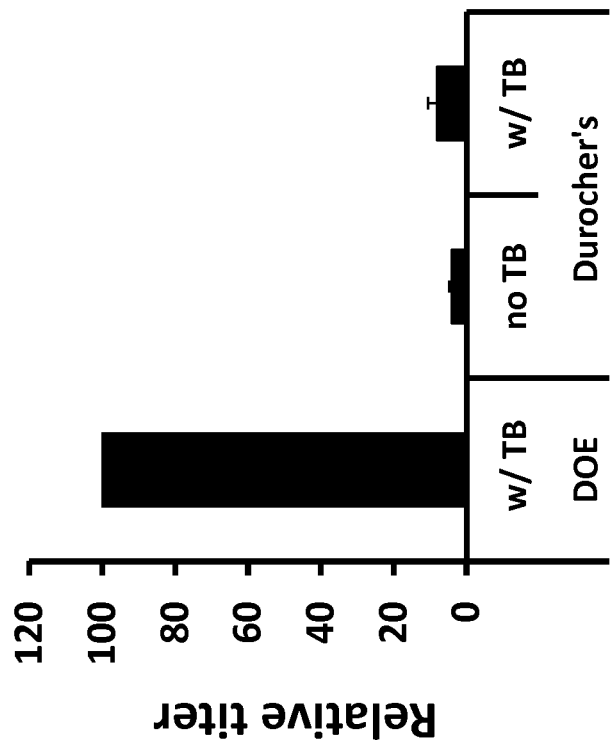
FIG. 10A-B shows a comparison of rAAV vector production (rAAV2 in FIG. 10A; rAAV2/8 in FIG. 10B) yields using the DOE and Durocher's protocols. Durocher's protocol (Table 4) was followed, except suspension HEK293T cells and the pCis plasmid pAAV-LacZ were used and the cells were harvested at 72 h post transfection. Also, TN1 and Na butyrate ("TB") were added to one experimental group of Durocher's protocol to evaluate the effects of TN1 and sodium butyrate on rAAV vector production using Durocher's protocol. The bars represent the average of duplicates.
Figure 10B:
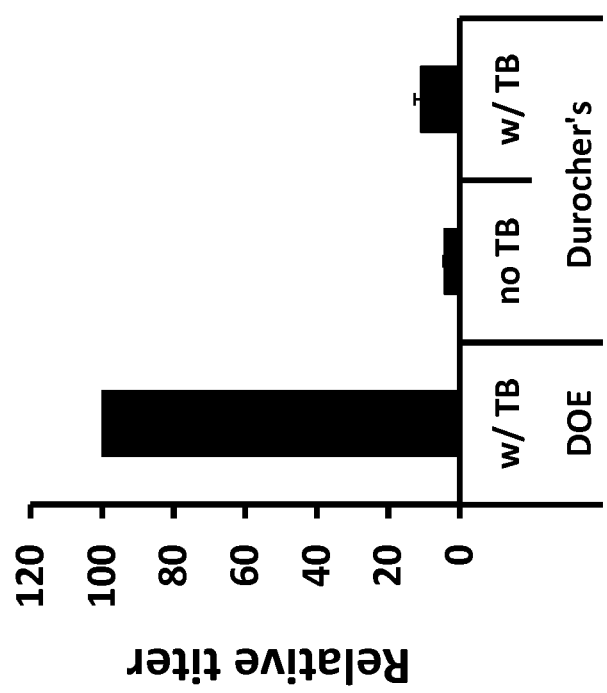

To eliminate the differences that might result from use of different cell lines in our and Durocher's protocols, 293T cells were used in both experiments. Also, in Durocher's method, the virus was harvested at 48 hrs to achieve maximum IVP, while we typically harvest at 72 hrs and use total GC as an index for production. To normalize the result interpretation, rAAV vectors produced using both protocols were harvested at 72 hrs to compare the yields using GC titration. In addition, experiments using Durocher's method were carried out with or without addition of TN1 and sodium butyrate, since our DOE-improved protocol included the addition of TN1 and sodium butyrate. The results showed that Durocher's protocol yielded approximately 5% and 11% of the total GC produced using the DOE-improved protocol without and with the additives, respectively (FIGS. 10A and 10B).

9. Protein hydrolysate (e.g., TN1) is critical for rAAV vector production using the DOE-improved protocol. The concentrations of additivesTN1 and sodium butyrate were not optimized at the time of the DOE analysis to keep the number of runs at a manageable level. Instead, we employed the concentration of TN1 (0.5%) that is commonly used in recombinant protein production and the concentration of sodium butyrate (5 mM) used in our OFAT-protocol for rAAV2/5 vector production. To verify the effects of TN1 and sodium butyrate in rAAV2/8 vector production using the DOE-improved protocol, TN1 and sodium butyrate were removed or added separately to the cells, and the vector production was evaluated by quantifying capsid protein levels in lysates by Immunoblot. No capsid protein was detected in the absence of TN1, suggesting a critical role for TN1 in the newly established protocol. Addition of sodium butyrate further increased AAV capsid protein expression (data not shown). Therefore, a second DOE-optimization was pursued to optimize the concentrations of TN1 and sodium butyrate with the range of TN1 from 0-2% and sodium butyrate from 0-20 mM (Table 5, below).

TABLE 5

DOE-optimization to optimize the concentrations of TN1 and sodium butyrate.

| Additives | Range of DOE | Optimal concentration | 90% of optimal | Experimental susp. Conditions rAAV2/5 (OFAT)$ |
|---|---|---|---|---|
| TN1 (% w/v)$ | 0-2 | 1.5 | 1.475-1.525 | 0.5 |
| Sodium butyrate (mM)$ | 0-20 | 0 | 0-1 | 5 |

$Pham et al, Biotechnol Bioeng, 90: 332-344, 2005, Palermo et al., J Biotechnol. 19: 35-47, (1991) and Zhao et al. Mol. Ther. 19 Supplement 1: S257 (2011).

Figure 11C:
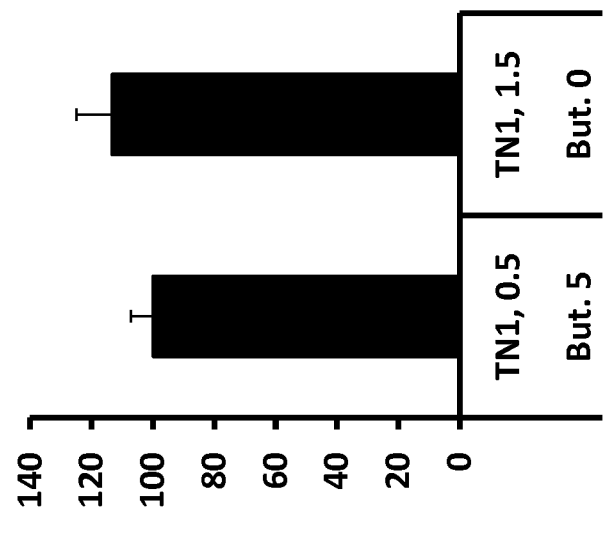
Figure 11B:
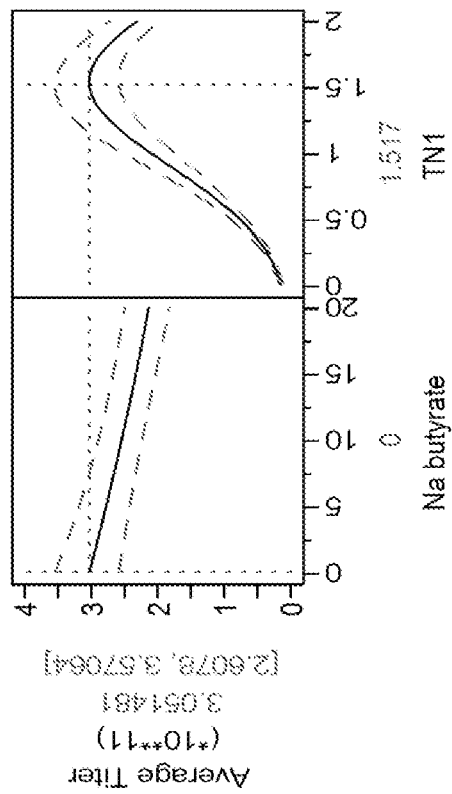
Figure 11D:
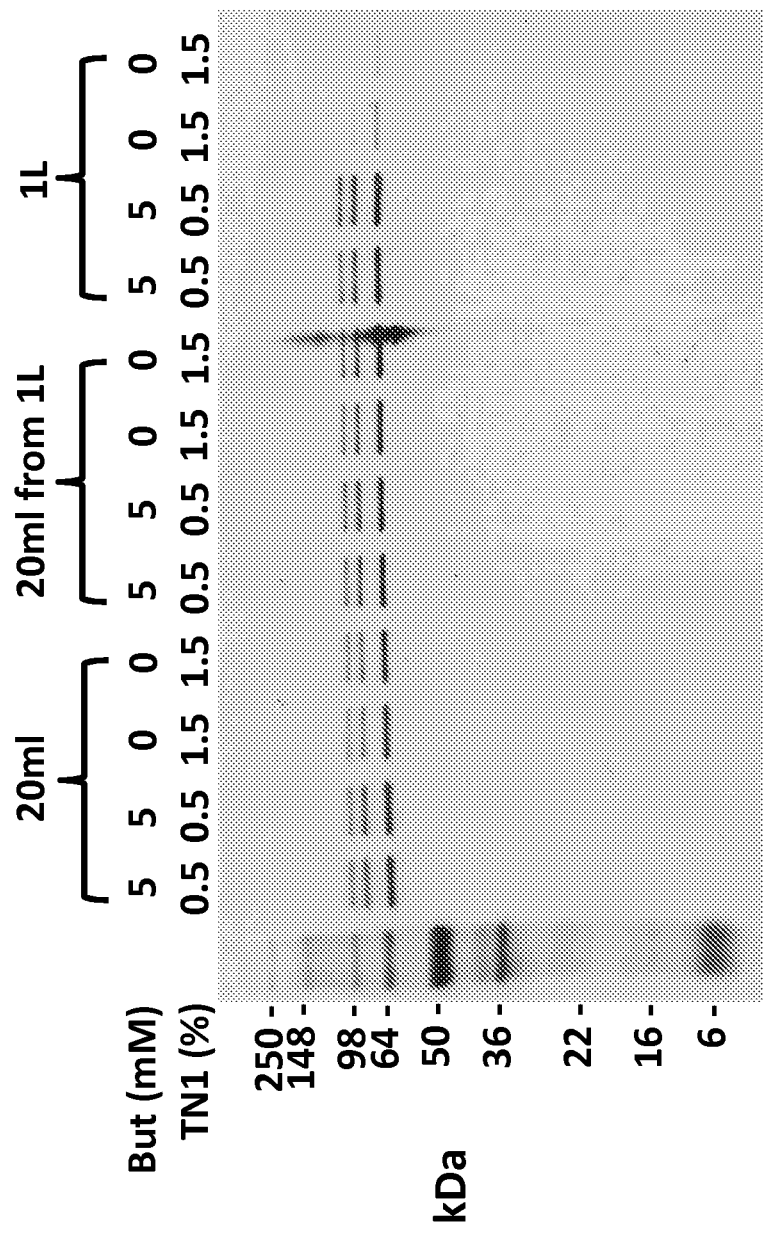
Figure 11E:
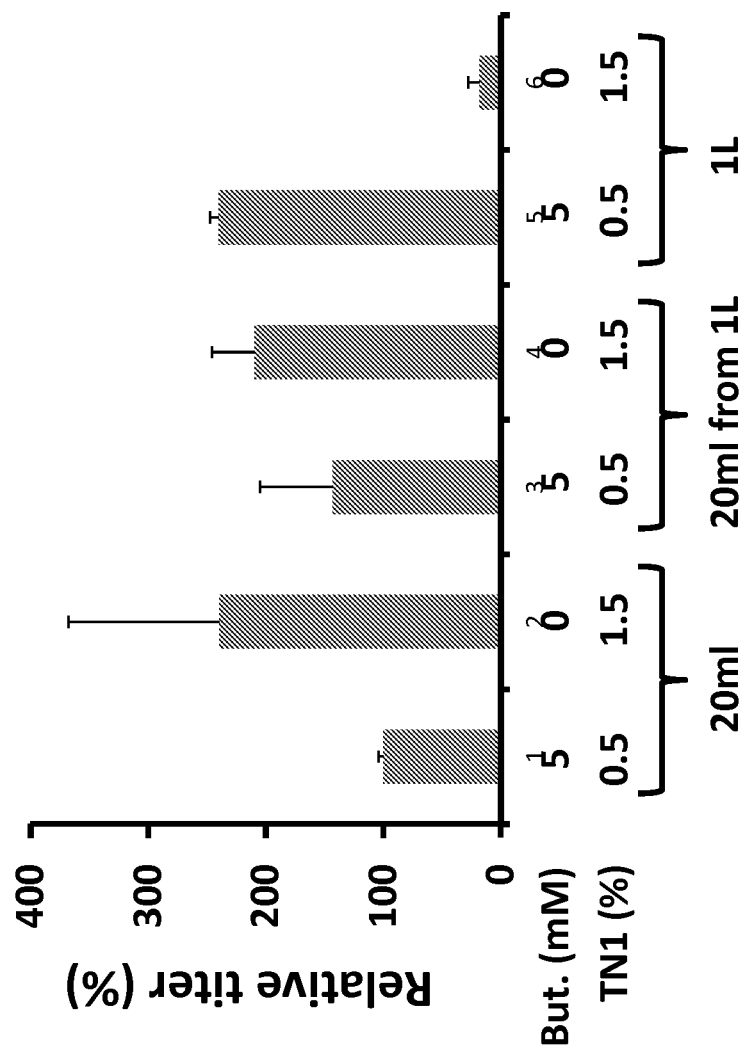

In this experiment, the concentration of GC per liter from cell lysates was determined by bDNA assay (FIG. 11A), and we confirmed that TN1 is critical in rAAV2/8 vector production. The results from the experiment were analyzed by the computer program and the prediction profile showed that the optimal TN1 concentration is 1.5% (w/v) and that sodium butyrate is unnecessary for rAAV2/8 vector production (FIG. 11B). This new identified optimal condition was compared with the previously used TN1 and sodium butyrate concentrations (FIG. 11C) and we found that a similar amount of rAAV2/8 vectors was produced under the protocols where sodium butyrate was both absent and present, indicating that sodium butyrate is not necessary. However, when these optimal conditions were applied to large scale (1-L) of rAAV2/8-empty vector production (rAAV2/8 does not carry GOI), much less rAAV vectors by 10-folds were obtained as compared to small scale culture (20 ml) (FIG. 11D-E). In this study, 20 ml of cells were also removed from 1-L culture immediately after transfection and cultured in a 125 ml flask to rule out any cell density and transfection variations (20 ml from 1 L). Twenty-four hours post transfection, different amount of TN1 and sodium butyrate were added to the culture. rAAVs were then purified, analyzed and titrated by silver stain and bDNA assay (FIG. 11D and FIG. 11E). It is evident that production with DOE optimized condition (TN1=1.5% w/v) is as efficient as the conditions before optimization (TN1=0.5% w/v, sodium butyrate=5 mM) in small scale, but not in 1-L culture. The cause for this is not clear, but it could be due to culture conditions between small scale (in 125-ml flask with shacking speed 110 rpm) and large scale (in 3-L flask with shacking speed 65 rpm. Therefore, rAAV vector production in the presence of sodium butyrate (TN1=0.5% w/v and sodium butyrate=5 mM) was more optimal for large scale rAAV virion production.

Interestingly, as shown in Table 2 (above), the values identified for two parameters, cell density and plasmid ratios, are notably different from the previously reported values identified via optimization with the OFAT method. Using the OFAT method, we and others (Zhao H, Wolf T, van der Valk M, Plewa C A, Sheng J, Lee K J. Cost effective and facile method of rAAV production in suspension-adapted HEK293 cells. Mol. Ther. 19, Supplement 1:S257 (2011)), and Durocher Y, Pham P L, St-Laurent G, Jacob D, Cass B, Chahal P, Lau C J, Nalbantoglu J, Kamen A. Scalable serum-free production of recombinant adeno-associated virus type 2 by transfection of 293 suspension cells. J. Virol. Methods. 144:32-40 (2007)) observed that, when the DNA amount is kept constant, higher cell density resulted in decreased yield. In contrast, the DOE approach projected an optimal cell density of 2.45×106 cells/ml, which was approximately 2.5 to 5-times higher than that obtained from OFAT methods while a similar amount of DNA (1.5 mg/ml) was projected, suggesting that the interaction between parameters plays an important role in rAAV2/8 vector production.

Another striking difference between the DOE-improved values and previously identified parameter values was the plasmid ratio. The plasmid ratio from the DOE optimization has a very high proportion of pTrans, as shown in Table 2 (1:5:0.31). This translates to pTrans (encoding the cap and rep genes) making up approximately 80% the total DNA used. Vincent, et al. reported that capsid formation is the rate-limiting step in rAAV vector production (Vincent, K A et al., Analysis of recombinant adeno-associated virus packaging and requirements for rep and cap gene products. J. Virol. 71:1897-905 (1997)). In fact, 40% more rAAV particles were produced when a plasmid encoding the cap gene under control of the CMV promoter was co-transfected (Hildinger, M et al., High-titer, serum-free production of adeno-associated virus vectors by polyethyleneimine-mediated plasmid transfection in mammalian suspension cells, Biotechnol. Lett. 29:1713-21 (2007)). The very high proportion of pTrans revealed by DOE-optimization could reflect the fact that higher cap gene expression driven by the high concentration of pTrans plasmid overcomes the rate-limiting step in rAAV vector production. In addition, the ratio of 1:5:0.31 uses less pHelper and pCis-GOI, especially pCis-GOI, than that used in previously reported protocols. The amount of pCis-GOI is approximately 4-fold lower in absolute amount than that used in previously reported protocols (Durocher, Y et al., Scalable serum-free production of recombinant adeno-associated virus type 2 by transfection of 293 suspension cells. J Virol Methods. 144:32-40 (2007); Hildinger, M et al., High-titer, serum-free production of adeno-associated virus vectors by polyethyleneimine-mediated plasmid transfection in mammalian suspension cells, Biotechnol. Lett. 29:1713-21 (2007)).

We show for the first time that a proportionally large amount of pHelper and pCis-GOI is not necessary in rAAV vector production in either adherent or suspension cells. This seems to contrast with the results from the OFAT optimization by Durocher's group in HEK 293E cells (Durocher Y, et al., Scalable serum-free production of recombinant adeno-associated virus type 2 by transfection on 293 suspension cells, J. Virol. Methods 144:32-40 (2007)), which showed that a higher level of pHelper is important in rAAV2 vector production in 293E cells. For adherent cells, the plasmid ratio was also optimized using the OFAT method in HEK 293 cells, and a higher proportion of pHelper (60%) was found to be optimal (Xiao X, Samulski R J. Production of high-titer recombinant adeno-associated virus vector in the absence of helper adenovirus. J. Virol. 72:2224-2232 (1998)). The reason for the difference between our observation and previous reports is currently not clear, but could be due to the different optimization methods employed. In addition, the lower amount of pHelper needed in the protocol will alleviate the burden of large-scale pHelper DNA purification using anion exchange chromatography which is problematic because the large size of the pHelper plasmid makes elution from the column difficult. Moreover, in the DOE optimized protocol, only about 5% of the standard amount of pCis-GOI was needed. This facilitates screening large number of GOIs in vivo since the amount of each GOI plasmid required can be significantly reduced. The reduction of the required amount of both pHelper and pCis-GOI alleviates resources required for rAAV vector production. Furthermore, we showed that the DOE-improved plasmid ratio and DNA amount was successfully applied to adherent HEK 293T cells, which resulted in significant reduction of the total amount of DNA, and the amount of pHelper and pCis-GOI. This implies that the optimized plasmid ratio could be applied to rAAV production regardless of culture modes (adherent or suspension), serotype or other rAAV plasmid system.

We used suspension HEK 293T cells for the optimization of rAAV2/5 and rAAV2/8 vector production due to its higher transfection efficiency than that of 293-6E (Zhao, H et al., Cost effective and facile method of rAAV production in suspension-adapted HEK293 cells, Mol. Ther. 19, Supplement 1:S257 (2011)). As shown in FIG. 9, suspension HEK293T cells produced a higher number of rAAV vector particles by approximately 3-fold or 5-fold in rAAV2/8 and AAV2 vectors production than that of HEK293-6E cells, respectively. The higher production yield is likely due to the higher transfection efficiency (data not shown).

It was unexpected that fewer rAAV2 vectors were produced by Agilent's plasmids using DOE-improved conditions. This could be due to a difference in the pTrans plasmids in that our pTrans was obtained through extensive modification and optimization upstream of the rep ORF in order to enhance AAV cap gene expression. The modification might reduce the rep gene expression, and could facilitate both the cap gene expression and rAAV vector production as high rep gene expression has been reported to inhibit the production of rAAV vectors (Vincent, K A et al., Analysis of recombinant adeno-associated virus packaging and requirements for rep and cap gene products. J. Virol. 71:1897-905 (1997)). The fact that fewer rAAV2 vectors were produced when our pTrans2 was replaced with published pACG2 and pXX2 while using the same pHelper and pCis-EGFP (FIG. 8A-C) implies that the configuration of pTrans may also play a role in rAAV vector production yields.

TN1 and sodium butyrate were used throughout our optimization process because higher capsid protein expression was achieved by using these additives in our previous optimization (Zhao, H et al., Cost effective and facile method of rAAV production in suspension-adapted HEK293 cells, Mol. Ther. 19, Supplement 1:S257 (2011)) and it was previously reported that TN1 addition increased rAAV2-EGFP production by 30% (Hildinger, M. et al., High-titer, serum-free production of adeno-associated virus vectors by polyethyleneimine-mediated plasmid transfection in mammalian suspension cells, Biotechnol. Lett. 29:1713-21 (2007)). The roles of TN1 and sodium butyrate in the DOE optimized protocol were examined again and the results indicated that TN1 played a critical role in rAAV vector production. In contrast, sodium butyrate was not necessary (FIG. 11A-C) although that was not the case in our OFAT-optimized protocol (data not shown). The underlying mechanism of TN1 in rAAV vector production is not clear. However, TN1 has been reported to increase both the mRNA and recombinant protein expression levels, suggesting it might act at both transcriptional and translational levels (Pham, P L et al., Transient gene expression in HEK293 cells: peptone addition posttransfection improves recombinant protein synthesis. Biotechnol Bioeng. 90:332-44 (2005)).

In an attempt to compare rAAV vector production yields of both DOE-improved and published OFAT-optimized protocols, Durocher's protocol was chosen for comparison due to its simplicity and similarity to our procedure (Durocher, Y et al., Scalable serum-free production of recombinant adeno-associated virus type 2 by transfection of 293 suspension cells. J Virol Methods. 144:32-40 (2007)). Unexpectedly, much lower amounts of rAAV2 and rAAV2/8 vectors were produced using Durocher's protocol (<5%) as compared to the DOE-improved protocol. This implies that optimization using the DOE method is superior to OFAT and that pTrans plays an important role in efficient rAAV vector production.

Figure 12A:
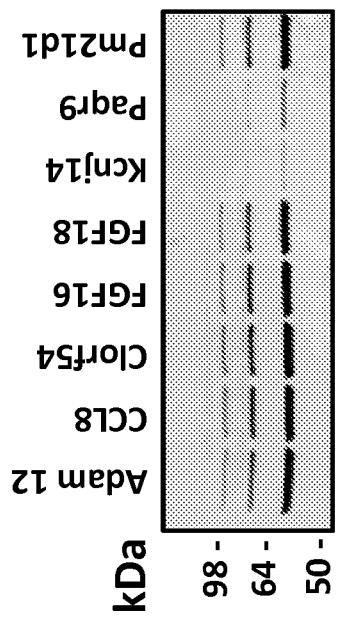
FIG. 12A shows an immunoblot analysis of AAV cap expression. HEK293T cells (1 liter) were transfected with pHelper, pTrans and various pCis-GOIs using the DOE-optimized method described in Example 2. Three days after transfection, cells and conditioned medium were harvested. Harvested rAAV vectors were separated on 4-20% SDS-PAGE. AAV capsid proteins were detected by immunoblot with anti-VPs antibody (Fitzgerald Industries International, Inc., Acton, Mass., cat. #10R-A114a). Molecular weight markers are indicated on the left and esxperessed GOIs are indicated on top of the gel.
Figure 12B:
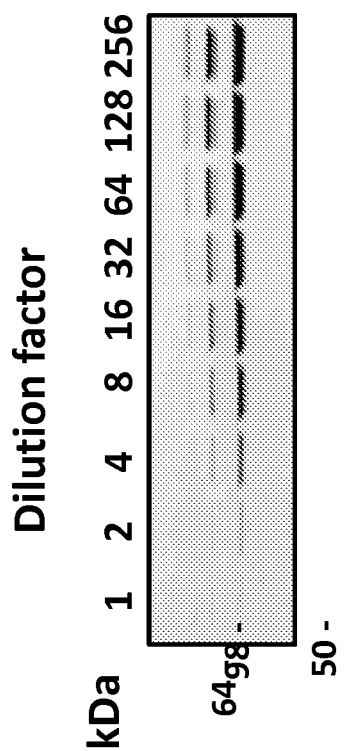
FIG. 12B-C show that lowering the amount of pCis-Kcnj14 resulted in increased AAV cap expression and greater yields of rAAV8-Kcnj14 vector. HEK293T cells (20 ml batch cultures) were transfected with fixed DOE-optimized amounts of pHelper, and pTrans, and various amounts of pCis-Kcnj14 (1 to 1/256 of the DOE-optimized amount) using the DOE-optimized protocol described in Example 2. After 3 days, cells and medium were harvested for analysis.
Figure 12C:
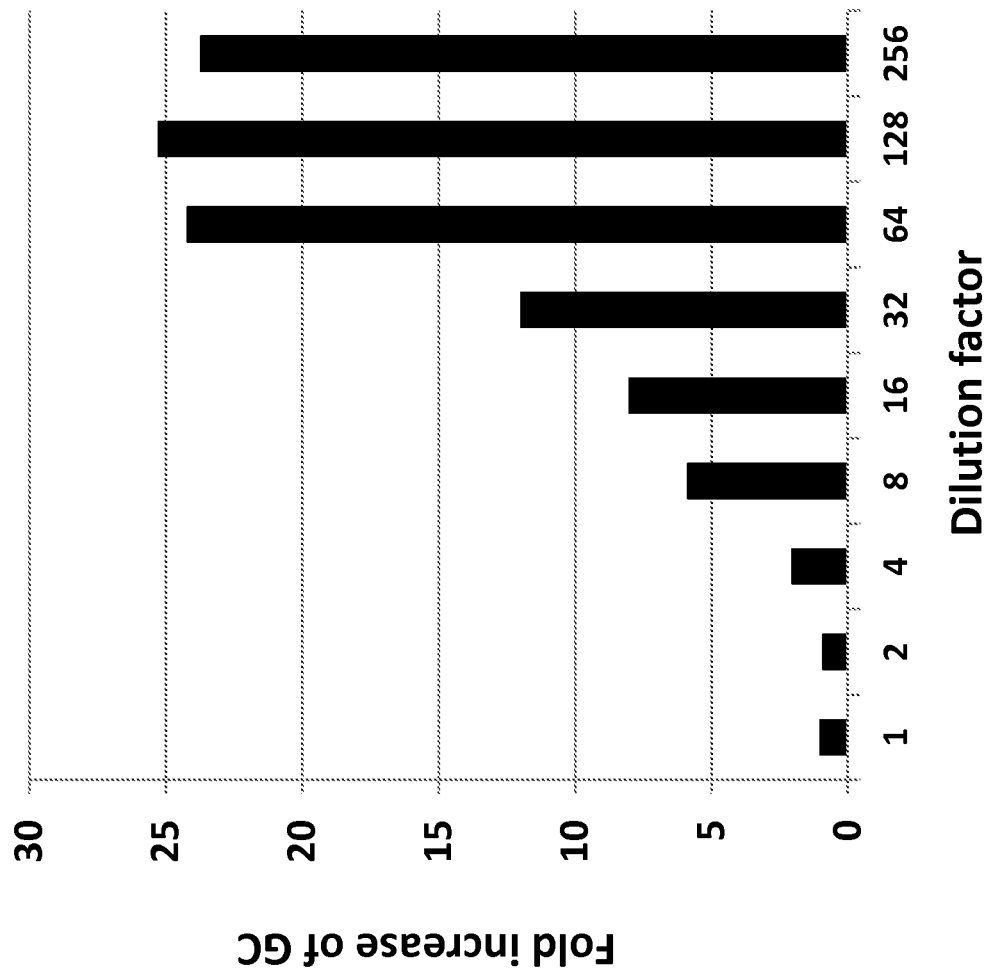
Figure 12E:
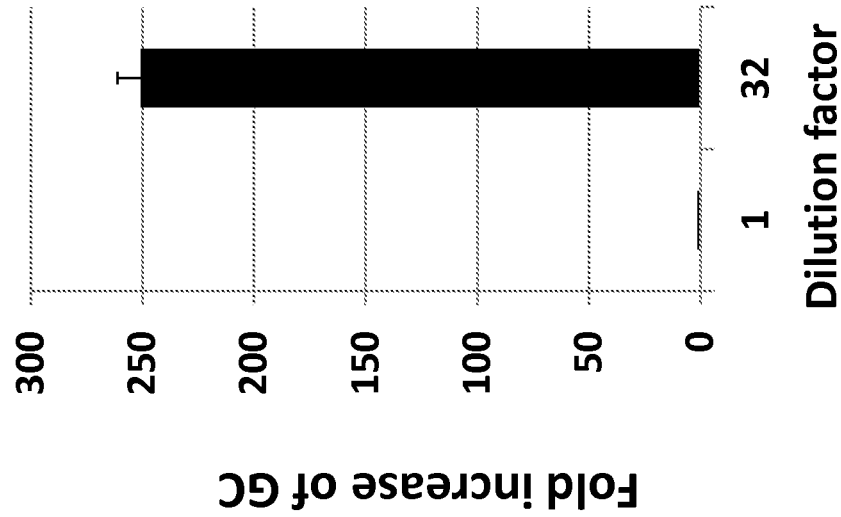
FIG. 12E illustrates that decreasing the amount of pCis-Kcnj14 dramatically increased the production yield of rAAV-Kcnj14. HEK293T cells (1 liter batch culture) were transfected with fixed amounts of DOE-optimized pHelper and pTrans, and various amounts of pCis-GOIs (1 and 1/32) with the DOE-optimized method described in Example 2. Three days after transfection, cells and conditioned medium were harvested. Harvested rAAV vectors were purified and quantified by the method described in FIG. 12D above. Dilution factors of pCis-Kcnj14 are indicated at the bottom.
Figure 12D:
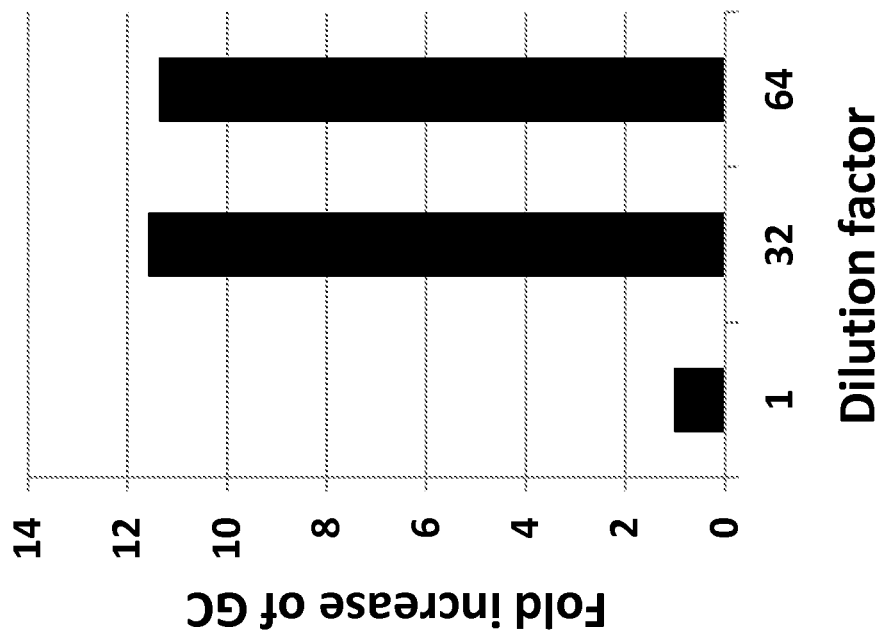
FIG. 12D illustrates that decreasing the amount of pCis-Paqr9 dramatically increased the production yield of rAAV-Paqr9 vector. HEK293T cells (1 liter batch culture) were transfected with fixed DOE-optimized amount of pHelper and pTrans, and various amounts of pCis-GOIs (1, 1/32 and 1/64) using the DOE-optimized protocol described in Example 2. Three days after transfection, cells and conditioned medium were harvested. Harvested rAAV vectors were purified by AVB-Sepharose chromatography and the GC of purified rAAV were determined by the CyQant fluorescent method (Cell Biolabs, Inc.). Dilution factors of pCis-Paqr9 are indicated at the bottom.

When yields of rAAV vector production for a particular GOI are much lower than that of average production yields, these poor yields can be dramatically increased by further decreasing the DOE-optimized amount of pCis plasmid. FIG. 12A shows that the yields of some rAAV vectors (rAAV8-Kcnj14 and -Paqr9) can be very low as compared to other rAAV vectors produced under the same conditions. In the experiment, rAAV vectors were produced in 1-liter cultures by triple transfection using DOE-optimized conditions as described in Example 2 above and pHelper, pTrans2/8 and pCis encoding the GOIs. After 72 hours, transfected cells and conditioned media containing rAAV vectors were harvested and AAV cap expression was analyzed by immunoblot analysis using anti-VP antibody (Fitzgerald Industries International, Inc., Acton, Mass., cat. #10R-A114a). The amino acid sequences of the C-terminal ends of AAV VP1, VP2, and VP3 are identical; the anti-VP antibody recognizes the peptide sequence of the C-terminus (726-733) that is common for all 3 VPs. FIGS. 12B and 12C show that the AAV cap expression (B) and GC (genome copies, C) of rAAV8-Kcnj14 significantly increased with the decreased amount of pCis-Kcnj14. In the experiment, rAAV8-Kcnj14 was generated in 20-mL cultures using DOE-optimized conditions with two times serial dilutions of pCis-Kcnj14 from 1 (DOE-optimized amount) to 256 times ($\frac{1}{256}$ of DOE-optimized amount). After harvest, VPs and GCs were analyzed by immunoblot (FIG. 12B) and CyQuant fluorescent method (FIG. 12C) after rAAV vector purification, respectively; FIG. 12D and FIG. 12E show that yields of rAAV8-Paqr9 and rAAV8-Kcnj14 dramatically increased using $\frac{1}{32}$ or $\frac{1}{64}$ of the amount of DOE-optimized pCis. These two rAAVs were produced in 1-liter culture using DOE-optimized conditions (1) and reduced amount of pCis ($\frac{1}{32}$ or $\frac{1}{64}$). The produced rAAV8 vectors were purified with AVB-Sepharose and quantified by CyQuant fluorescent method.

It appears that the production yields of rAAV vectors may significantly differ for different pCis-GOIs, though the DOE-optimized methods are applied to the rAAV vector production under the same conditions. As shown in FIG. 12A, although these eight different rAAV vectors were produced using the DOE-improved protocol, the amount of AAV cap expression (therefore, it correlated with the yield of rAAV vector production) co-transfected with some genes such as Kcnj14 Paqr9, were very low as compared to other genes (FIG. 12A). Since GOI can be expressed by the pCis-GOI plasmid, we speculated that the decreased rAAV vector production could be caused by the gene product of GOI. Thus, the pCis-Kcnj14 was serially diluted from 1 (amount of DOE-improved protocol) to 256 times for rAAV vector production in 20-mL culture, and the AAV cap expression and rAAV GCs were monitored. FIG. 12B and FIG. 12C show that, following the dilution of pCis plasmid, both AAV cap protein expression and the yield of rAAV-Kcnj14 significantly increased, which was further confirmed by large scale (1-liter) production of these rAAVs (FIG. 12D and FIG. 12E). These results show that yields of rAAV8-Paqr9 and rAAV8-Kcnj14 were increased dramatically by using $\frac{1}{32}$ or $\frac{1}{64}$ amounts of pCis. GOI expression is a byproduct of rAAV vector production and not necessary for generating rAAV vectors. Furthermore, GOI products could affect rAAV vector production, depending on the function of the GOI. The results showed here indicate that, in some cases, GOI expression can be destructive for rAAV vector production. Thus, reduction of pCis plasmid and, therefore, reduction of GOI expression can be beneficial to the yield of rAAV vector production.

What is claimed:

1. An in vitro method of producing a recombinant AAV virion in a mammalian host cell, wherein the mammalian host cell is a HEK 293 cell, and wherein the cell is suspended in a transfection media, comprising contacting the cell with polyethylenimine ("PEI") and:
   (i) an accessory construct, wherein said accessory construct is a plasmid (pHelper) consisting essentially of adenoviral E2, E4Orf6, and VAI RNA genes operably linked to an origin of replication element and one or more other regulatory sequences;
   (ii) an AAV helper construct, wherein said AAV helper construct is a plasmid (pTrans) consisting essentially of AAV2 rep and AAV1, AAV2, AAV5, AAV8, or AAV9 cap coding regions operably linked to one or more regulatory sequences; and
   (iii) an AAV vector construct, wherein said AAV vector construct is a plasmid (pCis) consisting essentially of AAV2 inverted terminal repeats flanking a heterologous gene of interest operably linked to one or more regulatory sequences,
wherein the ratio of pHelper:pTrans:pCis is 1:5:(0.009-0.36) (weight:weight:weight), the PEI is Transfection Grade Linear Polyethylenimine Hydrochloride (MW 40,000), and the ratio of PEI:DNA is about 3:1.

2. The method of claim 1, wherein the HEK 293 cell is suspended at a cell density of $2.1$-$3.0 \times 10^6$ cells/mL.

3. The method of claim 2, wherein the HEK 293 cell is suspended at a cell density of $2.2$-$2.7 \times 10^6$ cells/mL.

4. The method of claim 3, wherein the HEK 293 cell is suspended at a cell density of about $2.5 \times 10^6$ cells/mL.

5. The method of claim 1, wherein the ratio of pHelper:pTrans:pCis is 1:5:(0.30-0.36) (weight:weight:weight).

6. The method of claim 5, wherein the ratio of pHelper:pTrans:pCis is 1:5:0.31 (weight:weight:weight).

7. The method of claim 1, wherein the total amount of plasmid does not exceed 1.5 mg/L of transfection media.

8. An in vitro method of producing a recombinant AAV virion in a mammalian host cell, wherein the mammalian host cell is a HEK 293 cell, and wherein the cell adheres to a solid substrate in a transfection media, comprising contacting the cell with calcium phosphate and:
   an accessory construct, wherein said accessory construct is a plasmid (pHelper) consisting essentially of adenoviral E2, E4Orf6, and VAI RNA genes operably linked to an origin of replication element and one or more other regulatory sequences;
   (ii) an AAV helper construct, wherein said AAV helper construct is a plasmid (pTrans) consisting essentially of AAV2 rep and AAV1, AAV2, AAV5, AAV8, or AAV9 cap coding regions operably linked to one or more regulatory sequences; and
   (iii) an AAV vector construct, wherein said AAV vector construct is a plasmid (pCis) consisting essentially of AAV2 inverted terminal repeats flanking a heterologous gene of interest operably linked to one or more regulatory sequences, wherein the ratio of pHelper:pTrans:pCis is 1:5:(0.009-0.36) (weight:weight:weight).

9. The method of claim 8, wherein the HEK 293 cell is seeded at a cell density of $2.1\text{-}3.0\times10^6$ cells/mL.

10. The method of claim 2, wherein the HEK 293 cell is seeded at a cell density of $2.2\text{-}2.7\times10^6$ cells/mL.

11. The method of claim 3, wherein the HEK 293 cell is seeded at a cell density of about $2.5\times10^6$ cells/mL.

12. The method of claim 1, wherein the ratio of pHelper:pTrans:pCis is 1:5:(0.30-0.36) (weight:weight:weight).

13. The method of claim 5, wherein the ratio of pHelper:pTrans:pCis is 1:5:0.31 (weight:weight:weight).

14. The method of claim 1, wherein the total amount of plasmid does not exceed 1.5 mg/L of transfection media.

* * * * *

SEQUENCE LISTING

```
<160> NUMBER OF SEQ ID NOS: 2

<210> SEQ ID NO 1
<211> LENGTH: 66
<212> TYPE: DNA
<213> ORGANISM: Artificial Sequence
<220> FEATURE:
<223> OTHER INFORMATION: Signal Sequence
<220> FEATURE:
<221> NAME/KEY: CDS
<222> LOCATION: (1)..(66)

<400> SEQUENCE: 1 atg gac atg agg gtg ccc gct cag ctc ctg ggg ctc ctg ctg tgg      48
Met Asp Met Arg Val Pro Ala Gln Leu Leu Gly Leu Leu Leu Trp
1               5                   10                  15 ctg aga ggt gcg cgc tgt                                           66
Leu Arg Gly Ala Arg Cys
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic Construct

<400> SEQUENCE: 2

Met Asp Met Arg Val Pro Ala Gln Leu Leu Gly Leu Leu Leu Trp
1               5                   10                  15

Leu Arg Gly Ala Arg Cys
            20
```